United States Patent
Lu et al.

(10) Patent No.: US 10,900,053 B2
(45) Date of Patent: Jan. 26, 2021

(54) GENOME-MODIFIED RECOMBINANT ADENO-ASSOCIATED VIRUS VECTORS

(71) Applicant: University of Florida Research Foundation, Incorporated, Gainesville, FL (US)

(72) Inventors: Yuan Lu, Gainesville, FL (US); Chen Ling, Gainesville, FL (US); Arun Srivastava, Gainesville, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 63 days.

(21) Appl. No.: 15/526,952

(22) PCT Filed: Nov. 21, 2015

(86) PCT No.: PCT/US2015/062037
§ 371 (c)(1),
(2) Date: May 15, 2017

(87) PCT Pub. No.: WO2016/081927
PCT Pub. Date: May 26, 2016

(65) Prior Publication Data
US 2017/0356009 A1 Dec. 14, 2017

Related U.S. Application Data

(60) Provisional application No. 62/083,095, filed on Nov. 21, 2014.

(51) Int. Cl.
*C12N 15/86* (2006.01)

(52) U.S. Cl.
CPC .... *C12N 15/86* (2013.01); *C12N 2750/14122* (2013.01); *C12N 2750/14143* (2013.01); *C12N 2830/002* (2013.01)

(58) Field of Classification Search
CPC .................................................. C12N 15/86
See application file for complete search history.

(56) References Cited

U.S. PATENT DOCUMENTS

| | | | |
|---|---|---|---|
| 6,346,415 B1 | 2/2002 | Feldhaus et al. | |
| 8,574,583 B2 | 11/2013 | Kay et al. | |
| 2005/0106558 A1 | 5/2005 | Perabo et al. | |
| 2014/0341852 A1 | 11/2014 | Srivastava et al. | |

FOREIGN PATENT DOCUMENTS

| WO | WO 1998/009524 A1 | | 3/1998 | |
|---|---|---|---|---|
| WO | WO 2000/012741 | * | 3/2000 | ........... C12N 15/861 |
| WO | WO 2000/012741 A2 | | 3/2000 | |

OTHER PUBLICATIONS

McCarty DM (2008, Molecular Therapy, vol. 16(10), pp. 1648-1656). (Year: 2008).*
Zhong et al. (2008, PNAS, vol. 105(22), pp. 7827-7832). (Year: 2008).*
Machine Translation of Mehtali et al. 11 page PDF (Year: 2000).*
Partial Supplementary European Search Report for Application No. EP 15860554.3 dated May 14, 2018.
Ling et al., The role of glucocorticoid receptor signaling in adeno-associated virus 2 infection. Molecular Therapy. May 1, 2016;24(S1):S6.
Extended European Search Report for Application No. EP 15860554.3 dated Aug. 16, 2018.
International Search Report and Written opinion dated Feb. 23, 2016 for Application No. PCT/US2015/062037.
International Preliminary Report on Patentability dated Jun. 1, 2017 for Application No. PCT/US2015/062037.
Jayandharan et al., Activation of the NF-kappaB pathway by adeno-associated virus (AAV) vectors and its implications in immune response and gene therapy, Proc Natl Acad Sci U S A. Mar. 1, 2011;108(9):3743-8. doi: 10.1073/pnas.1012753108. Epub Feb. 14, 2011.
Jayandharan et al., Strategies for improving the transduction efficiency of single-stranded adeno-associated virus vectors in vitro and in vivo. Gene Ther 2008, 15:1287-93.
Ling C., The Development of Adeno-Associated Virus Serotype 3 Vector-based Potential Gene Therapy for Human Liver Cancer, Dissertation, University of Florida, Jun. 17, 2011, 129 pages.
Ling et al., #310 Development of Generation X Recombinant AAV Vectors for Human Gene Therapy, Molecular Therapy, May 2015, vol. 23, Suppl 1, pS125.
Ling et al., #5 Transduction of primary human hepatocytes in vitro and in humanized murine livers in vivo by recombinant AAV3 vectors, Molecular Therapy, May 2014, vol. 22, Supp 1, p. S2.
Ling et al., #704 Development of the D[+]-sequence-deleted ssAAV2 vectors: Enhanced transgene expression in vitro and in vivo, Molecular Therapy, May 2010, vol. 18, Suppl 1, p. S275.
Ling et al., Enhanced Transgene Expression from Recombinant Single Stranded D-Sequence-Substituted Adeno-Associated Virus Vectors in Human Cell Lines in Vitro and in Murine Hepatocytes In Vivo, J of Virology, Jan. 2015, vol. 89, No. 2, pp. 952-961.
Lu et al., #706 Involvement of the glucocorticoid receptor signaling in AAV2 vector-mediated transgene expression, Molecular Therapy, May 2010, vol. 18, Suppl 1, p. S276.
Qi et al., Comparison of Transduction Efficiency of Tyrosine-Mutant AAV Serotype Vectors in Kidney, Clin Exp Pharmacol Physiol, Jan. 2013, vol. 40, No. 1, pp. 53-55.

(Continued)

*Primary Examiner* — Thaian N. Ton
*Assistant Examiner* — David A. Montanari
(74) *Attorney, Agent, or Firm* — Wolf, Greenfield & Sacks, P.C.

(57) ABSTRACT

Provided herein are recombinant adeno-associated virus (rAAV) nucleic acid vectors that comprise one or more modifications within at least one inverted terminal repeat (ITR) region. Exemplary modifications include ITR sequences comprising a glucocorticoid responsive element and/or a transcription factor binding site. Also provided are plasmids, libraries, rAAV particles, compositions, kits, and methods related to such vectors.

30 Claims, 13 Drawing Sheets

Specification includes a Sequence Listing.

(56) References Cited

OTHER PUBLICATIONS

Qing et al., Adeno-associated virus type 2-mediated gene transfer: role of cellular FKBP52 protein in transgene expression, J Virol, 2001, 75:8968-76.

Qing et al., Adeno-associated virus type 2-mediated gene transfer: correlation of tyrosine phosphorylation of the cellular single-stranded D sequence-binding protein with transgene expression in human cells in vitro and murine tissues in vivo, J Virol, 1998, 72:1593-9.

Qing et al., Role of tyrosine phosphorylation of a cellular protein in adeno-associated virus 2-mediated transgene expression, Proc Natl Acad Sci U S A, 1997,. 94:10879-10884.

Samulski et al., Rescue of adeno-associated virus from recombinant plasmids: gene correction within the terminal repeats of AAV, Cell, 1983, 33:135-143.

Strahle et al., A DNA sequence of 15 base pairs is sufficient to mediate both glucocorticoid and progesterone induction of gene expression. Proc Natl Acad Sci U S A, 1987, 84:7871-5.

Wang et al., Adeno-associated virus type 2 DNA replication in vivo: mutation analyses of the D sequence in viral inverted terminal repeats, J Virol, 1997, 71:3077-3082.

Wang et al., Rescue and replication of adeno-associated virus type 2 as well as vector DNA sequences from recombinant plasmids containing deletions in the viral inverted terminal repeats: selective encapsidation of viral genomes in progeny virions, J Virol, 1996, 70:1668-1677.

Wang et al., Rescue and replication signals of the adeno-associated virus 2 genome, J Mol Biol 1995, 250:573-580.

Zhao et al, Adeno-associated virus 2-mediated gene transfer: role of a cellular serine/threonine protein phosphatase in augmenting transduction efficiency, Gene Ther, 2007, 14:545-50.

Zhong et al., Efficient and targeted transduction of nonhuman primate liver with optimized AAV3B vectors through systemic delivery, ASGCT 17th Annual Meeting, 2014, 1 page.

Zhong et al., Single-polarity recombinant adeno-associated virus 2 vector-mediated transgene expression in vitro and in vivo: mechanism of transduction, Mol Ther, 2008, 16:290-295.

Zhou et al., Adeno-associated virus of a single-polarity DNA genome is capable of transduction in vivo, Molecular Therapy, 2008, 16:494-499.

\* cited by examiner

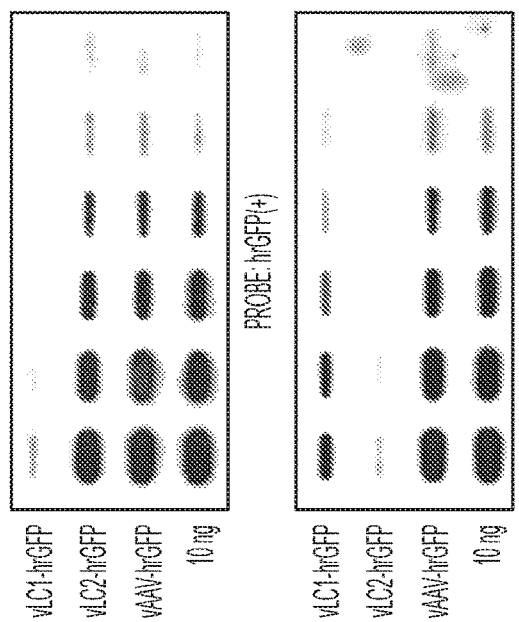
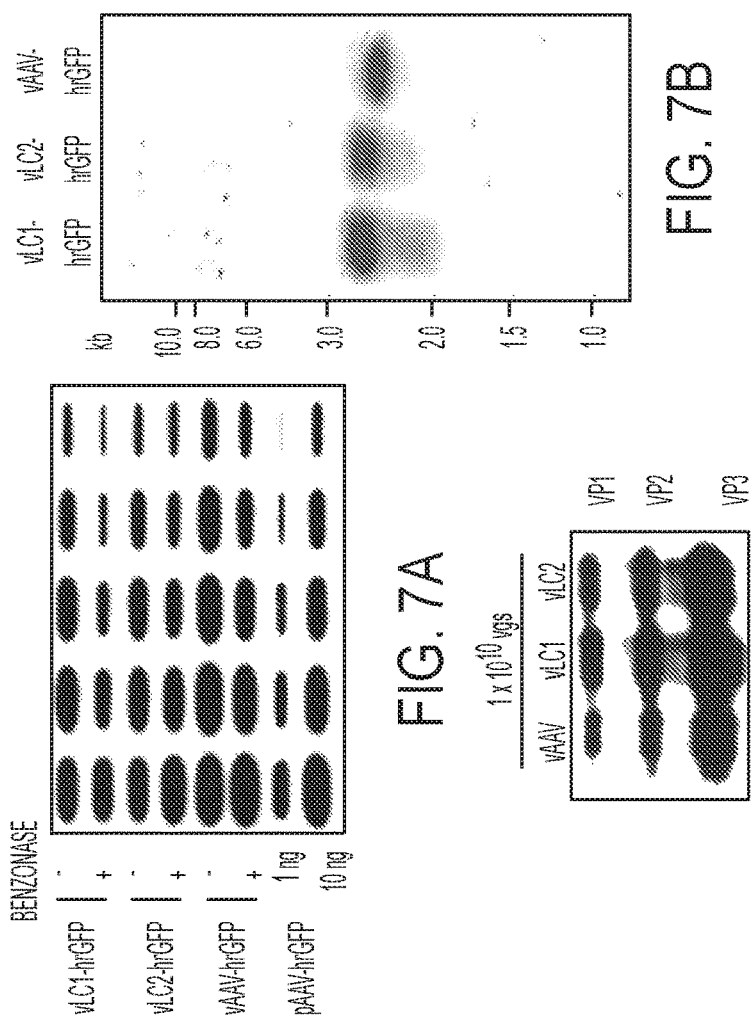
FIG. 7D
FIG. 7B
FIG. 7A
FIG. 7C

GENOME-MODIFIED RECOMBINANT ADENO-ASSOCIATED VIRUS VECTORS

CROSS-REFERENCE TO RELATED APPLICATIONS

The present application is a 35 U.S.C. § 371 National Phase Application of International Application No. PCT/US2015/062037, filed Nov. 21, 2015 and entitled "GENOME-MODIFIED RECOMBINANT ADENO-ASSOCIATED VIRUS VECTORS" which claims the priority benefit of U.S. Provisional Patent Appl. No. 62/083,095, filed Nov. 21, 2014 and entitled "GENOME-MODIFIED RECOMBINANT ADENO-ASSOCIATED VIRUS VECTORS", the entire contents of each of which are incorporated by reference herein.

FEDERALLY SPONSORED RESEARCH OR DEVELOPMENT

This invention was made with government support under DK-058327, HL-097088, and EB-015684 awarded by the National Institutes of Health. The government has certain rights in the invention.

BACKGROUND OF INVENTION

In general, gene therapy clinical trials performed to date have used recombinant adeno-associated virus (rAAV) vectors containing a single-stranded DNA genome, which is transcriptionally inactive, and thus negatively impacts the transduction efficiency of these vectors. There remains a need for improved rAAV vectors that overcome the issues associated with the relatively inactive genome in order to improve transduction efficiency.

SUMMARY OF THE INVENTION

Aspects of the disclosure relate, in part, to the development of rAAV vector genomes that comprise one or more modifications within the inverted terminal repeat (ITR) regions, such as within the D-sequences, which resulted in improved transduction efficiency. Accordingly, aspects of the disclosure relate to rAAV particles that contain genomes that comprise one or more modifications in an ITR region and plasmids comprising one or more modifications in an ITR region, e.g., that may be used to generate rAAV particles. In some embodiments, a recombinant adeno-associated virus (rAAV) particle, comprises a viral capsid encapsidating a nucleic acid vector, wherein the nucleic acid vector comprises a first inverted terminal repeat (ITR) sequence comprising a glucocorticoid receptor responsive element and/or a second ITR sequence comprising a transcription factor binding site. In some embodiments, a recombinant adeno-associated virus (rAAV) particle, comprises a viral capsid encapsidating a nucleic acid vector, wherein the nucleic acid vector comprises a first inverted terminal repeat (ITR) and a second ITR sequence, where only one of the ITRs comprises a full D-sequence. In some embodiments, the D-sequence that is removed (e.g., a D[+] or D[−] sequence) is replaced with a sequence that comprises one or more transcription factor binding sites that bind positive regulators of transcription (e.g., Foxd3 and/or NF-muE1). In some embodiments a D-sequence is replaced with a sequence that contains binding sites for both GATA-1 and/or GATA-2.

In some embodiments, the glucocorticoid receptor responsive element comprises the sequence GGTACANNNTGT(T/C)CT (SEQ ID NO: 1), wherein each N is independently a T, C, G or A and wherein (T/C) is either a T or a C nucleotide. In some embodiments, the transcription factor binding site is a transcription factor binding site for a transcription factor described in Table 1. In some embodiments, the nucleic acid vector further comprises a heterologous nucleic acid region comprising a sequence encoding a protein or polypeptide of interest or RNA of interest. In some embodiments, the protein or polypeptide of interest is a protein or polypeptide described in Table 2. In some embodiments, the viral capsid comprises a modified capsid protein comprising at least one mutation. In some embodiments, the modified capsid protein comprises at least one mutation described in Table 3. In some embodiments, the nucleic acid vector comprises the first ITR sequence and the second ITR sequence. In some embodiments, the nucleic acid vector is single stranded. In some embodiments, the nucleic acid vector is self-complementary.

In some embodiments, a plasmid comprises a first inverted terminal repeat (ITR) sequence comprising a glucocorticoid receptor responsive element and/or a second ITR sequence comprising a transcription factor binding site. In some embodiments, a plasmid comprises a first inverted terminal repeat (ITR) and a second ITR sequence, where only one of the ITRs comprises a full D-sequence. In some embodiments, the D-sequence that is removed (e.g., a D[+] or D[−] sequence) is replaced with a sequence that comprises one or more transcription factor binding sites that bind positive regulators of transcription (e.g., Foxd3 and/or NF-muE1). In some embodiments a D-sequence is replaced with a sequence that contains binding sites for both GATA-1 and/or GATA-2.

In some embodiments, the transcription factor binding site on the plasmid is a transcription factor binding site for a transcription factor described in Table 1. In some embodiments, the glucocorticoid receptor responsive element comprises the sequence GGTACANNNTGT(T/C)CT (SEQ ID NO: 1), wherein each N is independently a T, C, G or A and wherein (T/C) is either a T or a C nucleotide. In some embodiments, the plasmid further comprises a multiple cloning site, a promoter, and/or a heterologous nucleic acid region comprising a sequence encoding a protein or polypeptide of interest or RNA of interest. In some embodiments, the protein or polypeptide of interest is a protein or polypeptide described in Table 2.

In some embodiments, a kit comprises a rAAV particle described in this document.

In some embodiments, a method of delivering a nucleic acid vector to a cell comprises contacting a cell with a rAAV particle described in this document.

In some embodiments, the rAAV particle comprises the first inverted terminal repeat (ITR) sequence and the method further comprises contacting the cell with a glucocorticoid receptor (GR) activator. In some embodiments, the GR activator is dexamethasone. In some embodiments, the contacting is in vivo or in vitro.

In some embodiments, a library comprises a plurality of recombinant adeno-associated virus (rAAV) particles, each rAAV particle in the plurality comprises a viral capsid encapsidating a nucleic acid vector, wherein the nucleic acid vector comprises a first inverted terminal repeat (ITR) sequence comprising a glucocorticoid receptor responsive element and/or a second ITR sequence comprising a transcription factor binding site. In some embodiments, a library comprises a plurality of recombinant adeno-associated virus (rAAV) particles, each rAAV particle in the plurality comprises a viral capsid encapsidating a nucleic acid vector, wherein the nucleic acid vector comprises a first inverted terminal repeat (ITR) sequence and a second ITR sequence, wherein only one of the ITRs comprises a full D sequence. In some embodiments, the D sequence that is removed (e.g., a D[+] or D[−] sequence) is replaced with a sequence that comprises one or more transcription factor binding sites that bind positive regulators of transcription (e.g., Foxd3 and/or NF-muE1). In some embodiments a D-sequence is replaced with a sequence that contains binding sites for both GATA-1 and/or GATA-2.

In some embodiments, the viral capsid of each rAAV particle in the plurality comprises a modified capsid protein comprising at least one mutation.

In some embodiments, a library comprises a plurality of plasmids, each plasmid comprising a first inverted terminal repeat (ITR) sequence comprising a glucocorticoid receptor responsive element and/or a second ITR sequence comprising a transcription factor binding site. In some embodiments, a library comprises a plurality of plasmids, each plasmid comprising a first inverted terminal repeat (ITR) sequence and a second ITR sequence, wherein only one of the ITRs comprises a full D-sequence. In some embodiments, the D-sequence that is removed (e.g., a D[+] or D[−] sequence) is replaced with a sequence that comprises one or more transcription factor binding sites that bind positive regulators of transcription (e.g., Foxd3 and/or NF-muE1). In some embodiments a D-sequence is replaced with a sequence that contains binding sites for both GATA-1 and/or GATA-2.

In some embodiments, a nucleic acid vector comprises a first inverted terminal repeat (ITR) sequence comprising a glucocorticoid receptor responsive element and/or a second ITR sequence comprising a transcription factor binding site. In some embodiments, a nucleic acid vector comprises a first inverted terminal repeat (ITR) sequence and a second ITR sequence, wherein only one of the ITRs comprises a full D-sequence. In some embodiments, the D-sequence that is removed (e.g., a D[+] or D[−] sequence) is replaced with a sequence that comprises one or more transcription factor binding sites that bind positive regulators of transcription (e.g., Foxd3 and/or NF-muE1). In some embodiments a D-sequence is replaced with a sequence that contains binding sites for both GATA-1 and/or GATA-2.

In some embodiments, the transcription factor binding site is a transcription factor binding site for a transcription factor described in Table 1. In some embodiments, the glucocorticoid receptor responsive element comprises the sequence GGTACANNNTGT(T/C)CT (SEQ ID NO: 1), wherein each N is independently a T, C, G or A and wherein (T/C) is either a T or a C nucleotide. In some embodiments, the nucleic acid vector further comprises a multiple cloning site, a promoter, and/or a heterologous nucleic acid region comprising a sequence encoding a protein or polypeptide of interest or RNA of interest. In some embodiments, the protein or polypeptide of interest is a protein or polypeptide described in Table 2. In some embodiments, the nucleic acid vector is a single-stranded nucleic acid vector or a self-complementary nucleic acid vector.

The details of one or more embodiments of the disclosure are set forth in the description below. Other features or advantages of the present disclosure will be apparent from the following drawings and detailed description of several embodiments, and also from the appending claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 1A shows transduction efficiency of scAAV2 vectors in HeLa cells with treatment at various concentrations of dexamethasone (Dex). Cells were pre-treated with Dex for 12 hours, and infected with at an MOI of 2,000 vgs/cell of scAAV2-CBAp-EGFP vectors under identical conditions. Transgene expression was determined by fluorescence microscopy 72 hours post-infection. FIG. 1B shows the effect of GR activation by Dex treatment at different stages during infection with scAAV2 vectors. Group 1: no treatment; Groups 2-4: treatment either prior to, during, or post viral infection; Groups 5-7: combined treatment at any two stages; Group 8: treatment at all three stages. FIG. 1C shows the transduction efficiency of scAAV2 vectors in HeLa cells with treatment with 20 μM RU486. FIG. 1D shows the transduction efficiency of ssAAV2 vectors in HeLa cells with treatments with either Dex alone, Tyr23 alone, and Dex+Tyr23, and infected with at an MOI of 20,000 vgs/cell of ssAAV2-CBAp-EGFP vectors under identical conditions.

FIG. 2A shows transduction efficiency of scAAV vectors in U2OS cells. Cells were infected at various indicated MOI of scAAV2-CBAp-EGFP vectors under identical conditions. Transgene expression was determined by fluorescence microscopy 72 hours post-infection. FIG. 2B shows comparison of transduction efficiency of scAAV2 vectors in U2OS and U2OS+GR cells. Cells were infected with MOIs of 10,000 or 50,000 vgs/cell of scAAV2-CBAp-EGFP vectors under identical conditions, transgene expression was determined as described above. FIG. 2C shows transduction efficiency of scAAV2 vectors in U2OS and U2OS+GR cells with or without the treatment with Dex. Cells were pre-treated with Dex for 2 hours, and infected with at an MOI of 10,000 vgs/cell of scAAV2-CBAp-EGFP vectors under identical conditions.

FIG. 3A shows Electrophoretic mobility-shift assays (EMSAs) for GR binding. $^{32}$P labeled double-stranded oligonucleotides containing a conventional GRE site (GRE), AAV2 D-sequence (D), and a non-specific (NS) sequence were used as probes and incubated individually with the purified GR protein (Sigma) for 20 minutes at 25° C. and subjected to EMSA, in which the bound complexes were separated from the unbound probe on 6% polyacrylamide gels with 0.5×TBE buffer (pH 8.0) containing 89 mM Tris, 89 mM boric acid, 1 mM EDTA. Arrows indicate the bound complexes. FIG. 3B shows competition experiments using various indicated unlabeled oligonucleotides.

(FIG. 6A) Schematic structures of recombinant AAV genomes. HP: hairpin structure; D: D-sequence (SEQ ID NO: 2), S:

substitute sequence (SEQ ID NO: 3); CMVp: cytomegalovirus promoter; hrGFP: humanized recombinant green fluorescent protein; hGH (A)n: human growth hormone polyA signal. (FIG. 6B) Southern blot analysis for rescue and replication of AAV genomes from recombinant plasmids. (FIG. 6C) Southern blot analysis for the structural integrity of the replicative DNA intermediates containing substitutions in the D-sequence. Following digestion with or without Bgl II, the DNA fragments were analyzed by neutral agarose gel electrophoresis. (FIG. 6D) Schematic representation of structures of the replicative DNA intermediates of recombinant AAV genomes containing substitutions in the D-sequence. The monomeric (m) and dimeric (d) forms of replicative DNA intermediates, in both tail-to-tail (T-T) and head-to-head (H-H) configurations are depicted, the Bgl II restriction endonuclease restriction sites are denoted by arrowheads, and the predicted sized DNA fragments from each of the three plasmids are indicated. Southern blot analyses using a $^{32}$P-labeled DNA probe specific for hrGFP or hGH(A)n would detect the characteristic AAV replicative DNA intermediates generated from the three indicated plasmids. Following cleavage with Bgl II and probed with hrGFP, pLC1-hrGFP will generate only one band of 1.968 kb; pLC-2 will generate two bands of 2.155 kb and 4.310 kb, respectively; and pAAV-hrGFP will generate two bands of 2.110 kb and 4.220 kb, respectively. Following cleavage with Bgl II and probed with hGH(A)n, pLC1-hrGFP will generate two bands of 0.717 kb and 1.434 kb; pLC-2 will generate only one band of 0.530 kb; pAAV-hrGFP will generate two bands of 0.672 kb and 1.344 kb, respectively.

FIGS. 7A-D The effect of one D-sequence substitution on viral genome encapsidation. (FIG. 7A) Quantitative DNA slot-blot analyses for the efficiency of packaging of the rAAV genomes from the recombinant plasmids. The titer of each rAAV vector was determined by comparison with double-stranded, plasmid pAAV-hrGFP standards loaded onto the membrane. (FIG. 7B) Southern blot analysis of the nature of the rAAV DNA genomes in vector stocks. Equivalent volumes of DNA samples were denatured at 650° C. for 30 minutes and electrophoresed on alkaline agarose gels. (FIG. 7C) Western blot analysis of denatured viral capsids from vector stocks. (FIG. 7D) Quantitative DNA slot-blot analyses for determination of polarity of the mutant rAAV vector genomes. Two identical membranes were hybridized separately with one of the two complementary $^{32}$P-labeled oligonucleotides derived from the hrGFP plasmid. The hrGFP(+) (upper panel) or the hrGFP(−) (lower panel) probes hybridize with the minus-strand and the plus-strand of AAV DNA, respectively. The parental virus vAAV-hrGFP, which packages both strands, was included as a control.

(FIG. 9A) Comparison of transduction efficiencies of vLC1-, vLC2- and vAAV-hrGFP vectors in permissive cell lines (HEK293 and HeLa) and in less permissive cell lines (Huh7 and U2OS). Cells were infected with viral vectors at 2,000 vgs/cell for 2 hours. Transgene expression was determined by fluorescence microscopy 72 hours post-transduction. (FIGS. 9B and 9C) Fold changes in transgene expression mediated by vLC1-, vLC2- and vAAV-hrGFP vectors in HEK293 cells. Cells were infected with viral vectors at 2,000 vgs/cell for 2 hours, together with (B) treatment with either chemicals, or co-infection with adenovirus 2, or (C) transfection with the indicated plasmids. Transgene expression was determined by fluorescence microscopy 72 hours post-transduction. A change of 2.5-fold (horizontal line) was considered greater than the variability of the assay. (FIGS. 9D and 9E) Transduction efficiencies of vAAV-hrGFP, vLC1-hrGFP and vLC2-hrGFP vectors in HeLa and HEK293 cells, respectively. Cells were transduced with the vectors at 2,500 vgs/cell for 4 hours under identical conditions, and transgene expression was determined by flow cytometry 72 hours post-transduction. Both EGFP-positivity and mean fluorescence values are shown inset. (FIGS. 9F and 9G) Representative flow cytometry data from each group (n=3 for each cell type) are shown for HeLa and HEK293 cells, respectively.

(FIG. 10A) Schematic structures of recombinant AAV vector plasmids. CBAp: chicken β-actin promoter. (FIG. 10B) Bioluminescence imaging of mice injected with AAV2-Fluc vectors. C57BL/6 mice were injected with $1\times10^{10}$ vgs of either vAAV-Fluc (left panels), vLC1-Fluc (middle panels), or vLC2-Fluc (right panels). Images were acquired by a Xenogen IVIS® Imaging System 1 weeks or 8 weeks post-injection. Images of two representative animals from each group are shown. (FIG. 10C) The luminescence signal intensity was quantified as photons/second/cm2/steridian (p/s/cm2/sr) using the Living Image® software.

DETAILED DESCRIPTION OF THE INVENTION

Figure 1A:
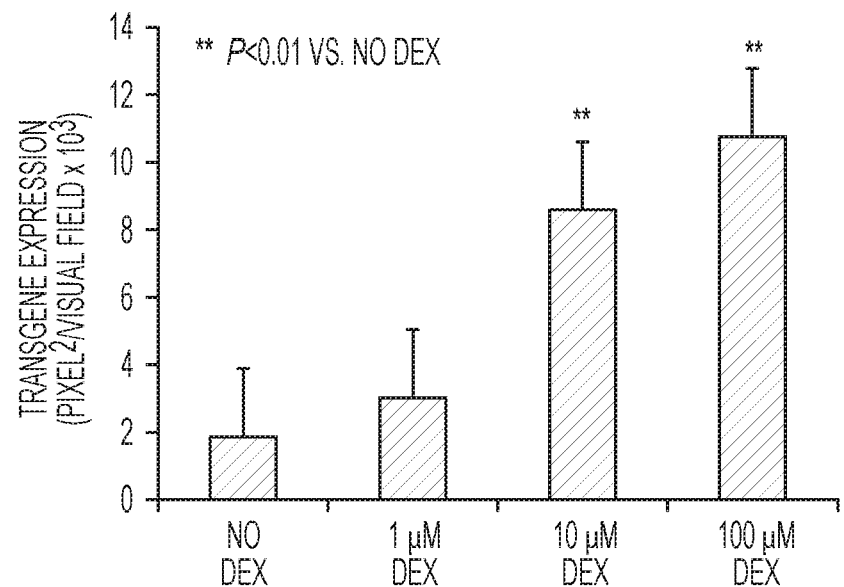
FIGS. 1A-D are series of graphs.

Aspects of the disclosure relate to rAAV particles, genomes, and plasmids, and their use in methods (e.g., therapeutic methods), libraries and compositions. Both wild-type and rAAV genomes contain inverted terminal repeats (ITRs) of about 145 nucleotides at both ends. The terminal 125 nucleotides in each ITR form a palindromic double-stranded T-shaped hairpin structure, in which the A-A' palindrome forms the stem, and the two smaller palindromes, B-B' and the C-C', form the cross-arms of the T. The other 20 nucleotides (D-sequence) in ITR remain single-stranded. The ssD[−] sequence is at the 3' end, whereas the complementary one, ssD[+] sequence is at the 5' end. Once in cells, the single-stranded virus undergoes second-strand DNA synthesis, which turns both ssD[−] and ssD[+] sequences into a double-stranded (ds) D [±] sequence.

The disclosure is based, in part, on modifications within the ITRs, more specifically within or involving the D-sequences. These modifications were shown to increase transduction efficiency and/or allow for regulatory control of one or more genes encoded by the nucleic acid vector. In one case, substitution of a D-sequence, which contained putative transcriptional repressor binding sites, with a sequence containing a different regulatory sequence, e.g., putative Foxd3 and NF-muE1 transcription enhancer binding sites, resulted in a dramatic increase in transduction efficiency. In another case, replacement of a partial glucocorticoid receptor responsive element (GRE) sequence within a D-sequence with a full GRE sequence enhanced transduction efficiency, which was further enhanced upon injection of the GR activator dexamethasone. Accordingly, aspects of the disclosure relate to rAAV particles containing nucleic acid vectors that contain one or more modifications to one or both ITRs, such as replacement of a D-sequence or a portion thereof with a GRE element and/or replacement of a D-sequence or a portion thereof with a transcription factor binding site and/or the removal of a D-sequence or a portion thereof. In some embodiments, the D-sequence that is removed (e.g., a D[+] or D[−] sequence) is replaced with a sequence that comprises one or more transcription factor binding sites that bind positive regulators of transcription (e.g., Foxd3 and/or NF-muE1). In some embodiments a D-sequence is replaced with a sequence that contains binding sites for both GATA-1 and/or GATA-2. The modifications are contemplated for use alone (e.g., a nucleic acid vector comprising replacement of a D-sequence or a portion thereof with a GRE element or replacement of a D-sequence or a portion thereof with a transcription factor binding site) or in combination (e.g., a nucleic acid vector comprising replacement of a D-sequence or a portion thereof with a GRE element and replacement of a D-sequence or a portion thereof with a transcription factor binding site). In some embodiments, a D-sequence or portion thereof in one of the ITRs is replaced with a GRE element and a D-sequence or portion thereof in the other ITR (at the other end of the rAAV genome) is replaced with a transcription factor binding site. Other aspects of the disclosure relate to the nucleic acid vectors or plasmids containing such modifications to one or both ITRs. Yet other aspects of the disclosure relate to compositions, libraries, kits and methods comprising such rAAV particles, nucleic acid vectors or plasmids.

In some embodiments, a recombinant adeno-associated virus (rAAV) particle is provided comprising a viral capsid encapsidating a nucleic acid vector, wherein the nucleic acid vector comprises a first inverted terminal repeat (ITR) sequence comprising a glucocorticoid receptor responsive element and/or a second ITR sequence comprising a transcription factor binding site. In some embodiments, a composition comprising a nucleic acid vector is provided, wherein the nucleic acid vector comprises a first inverted terminal repeat (ITR) sequence comprising a glucocorticoid receptor responsive element and/or a second ITR sequence comprising a transcription factor binding site. The nucleic acid vector may comprise either of the first ITR or second ITR sequence or it may comprise both ITR sequences. In some embodiments, the first ITR sequence is on the 5' end of the nucleic acid vector and the second ITR sequence is on the 3' end of the nucleic acid vector. In some embodiments, the first ITR sequence is on the 3' end of the nucleic acid vector and the second ITR is on the 5' end of the nucleic acid vector.

In some embodiments, an ITR sequence comprises:

(a) a sequence capable of forming a hairpin (e.g., comprising one or more palindromic regions (e.g., 3 palindromic regions) such as the exemplary sequence ttggc-cactccctctctgcgcgctcgctcgctcactgaggccgggcgac-caaaggtcgcccgacgcccgggctttgccc gggcggcctcagt-gagcgagcgagcgcgcagagagggagtggccaa (SEQ ID NO: 4) or a homolog thereof from any known AAV serotype) and (b) a D-sequence, in whole or in part, and/or any sequence that is replacing a D-sequence, in whole or in part, such as a glucocorticoid receptor responsive element and/or transcription factor binding site as described herein.

In some embodiments, a nucleic acid vector comprises one or more heterologous sequences (e.g., genes) encoding one or more proteins, polypeptides, or RNAs of interest in the intervening nucleic acid region between the two ITRs.

In some embodiments, the rAAV particle or nucleic acid vector is contained with a composition, such as a composition comprising a pharmaceutically acceptable carrier.

In some embodiments, a D-sequence within the first and/or second ITR sequence is replaced, in whole or in part, with the glucocorticoid receptor responsive element and/or the transcription factor binding site. Exemplary D-sequences include D[−]: 5'-AGGAACCCCTAGTGATGGAG-3' (SEQ ID NO: 5) and D[+]: 5'-CTCCATCACTAGGGGTTCCT-3' (SEQ ID NO: 6). However, other D sequences (e.g., for different AAV serotypes) may be modified as described in this document. In some embodiments, the first ITR comprising the glucocorticoid receptor responsive element further comprises a partial D-sequence. In some embodiments, the partial D-sequence is 5'-AGTGATGGAG-3' (SEQ ID NO: 7). In some embodiments, the replacement sequence (e.g., the glucocorticoid receptor responsive element and/or the transcription factor binding site) is the same length as or shorter than the D-sequence being replaced. In some embodiments, the replacement sequence is longer than the D-sequence. In this case, the size of the intervening nucleic acid region between the first ITR sequence and the second ITR sequence may be shorter. In some embodiments, the replacement sequence is added to the 5' end of the partial D-sequence. In some embodiments, the replacement sequence is added to the 3' end of the partial D-sequence. In some embodiments, a partial D sequence includes about 1-5, 5-10, 10-15, 15-19 nucleotides of the full D sequence (e.g., of the D(+) or the D(−) sequence).

In some embodiments, the glucocorticoid receptor responsive element comprises the sequence GGTA-CANNNTGT(T/C)CT (SEQ ID NO: 1), wherein each N is independently a T, C, G or A and wherein (T/C) is either a T or a C nucleotide. Other non-limiting, exemplary glucocorticoid receptor responsive elements include 5'-AGAA-CAnnnTGTTCT-3' (SEQ ID NO: 8) and 5'-GGCACAGTGTGGTCT-3' (SEQ ID NO: 9). Other glucocorticoid receptor responsive elements can be used, including for example glucocorticoid receptor responsive elements that are known in the art.

In some embodiments, removal of a D sequence involves a complete removal of the 20 nucleotides of the D sequence. However, in some embodiments a portion of one or both D sequences are removed (e.g., 1-5, 5-10, 10-15, 15-20, for example 15, 16, 17, 18, or 19, of one or both D sequences). In some embodiments, the removed D sequence(s) is (are) replaced with one or more sequences as described herein.

In some embodiments, the transcription factor binding site is a tissue-specific transcription factor binding site. Exemplary transcription factors are provided in Table 1. In some embodiments, the transcription factor binding site does not comprise the sequence TATTAGATCT-GATGGCCGCT (SEQ ID NO: 10) or the sequence CTC-CATCACTAGGGGTTCCT (SEQ ID NO: 6). Transcription factor binding sites are known in the art and can be identified using commercially and other publically available software or algorithms (see, e.g., Heinemeyer et al. 1998. Databases on transcriptional regulation: TRANSFAC, TRRD and COMPEL. Nucleic Acids Res 26:362-367., Marinescu et al. 2005. MAPPER: a search engine for the computational identification of putative transcription factor binding sites in multiple genomes. BMC Bioinformatics 6:79).

TABLE 1

Transcription Factors

| Transcription factor | Binding site consensus sequence or exemplary NCBI Genbank ID |
|---|---|
| POU3F2 | Gene ID: 5454 |
| FOXJ2 | Gene ID: 55810 |
| NR2E3 | Gene ID: 10002 |
| MEF-2 | Gene ID: 4205 |
| AP-1 | Gene ID: 3725 |
| Sp-1 | Gene ID: 6667 |
| KLF-4 | Gene ID: 9314 |
| GATA-6 | Gene ID: 2627 |
| HNF-1 | Gene ID: 6927 |
| MyOD | Gene ID: 4654 |
| C/EBP | Gene ID: 1050 |
| POU | Gene ID: 5460 |
| MRF | Gene ID: 745 |
| NKX2-5 | Gene ID: 1482 |
| GATA-4 | Gene ID: 2626 |
| GCM2 | Gene ID: 9247 |
| OTX-2 | Gene ID: 5015 |
| Pax-2 | Gene ID: 5076 |
| GATA-3 | Gene ID: 2625 |

In some embodiments, one of the two D-sequences (or portions thereof) can be substituted with any transcription factor binding site of interest. For example, a D-sequence can be substituted with a tissue specific transcription factor binding site to enhance transduction of a specific tissue, such as liver, brain, heart or retina.

In some embodiments, one or more GREs and/or transcription factor binding sites can be added to an rAAV nucleic acid (e.g., replacing one or both D-sequences or portions thereof in one or both ITRs or within the central nucleic acid region in between the ITRs, for example without replacing or modifying the D-sequences). In some embodiments, one or both D-sequences or portions thereof are replaced or modified to include one or more GREs and/or transcription factor binding sites. However, in some embodiments, one D-sequence or portion thereof is retained to provide necessary functions for the rAAV.

Other aspects of the disclosure relate to a library comprising a plurality of rAAV particle, nucleic acid vectors, or plasmids as described herein. In some embodiments, the library comprises a plurality of recombinant adeno-associated virus (rAAV) particles, each rAAV particle in the plurality comprises a viral capsid encapsidating a nucleic acid vector, wherein the nucleic acid vector comprises a first inverted terminal repeat (ITR) sequence comprising a glucocorticoid receptor responsive element and/or a second ITR sequence comprising a transcription factor binding site. In some embodiments, each member of the plurality comprises a distinct transcription factor binding site, optionally in combination with a modified capsid protein as described herein. In some embodiments, the library comprises a plurality of plasmids or nucleic acid vectors, wherein each plasmid or nucleic acid vector comprises a first inverted terminal repeat (ITR) sequence comprising a glucocorticoid receptor responsive element and/or a second ITR sequence comprising a transcription factor binding site. In some embodiments, each member of the plurality comprises a distinct transcription factor binding site. In some embodiments, each member of the plurality comprises a sequence encoding a detectable marker, such as a fluorescent protein or luciferase protein. Such libraries are useful, e.g., for screening rAAV particles to identify members of the library that transduce a cell or tissue of interest, such as a liver, brain, heart or retina cell or tissue. The libraries may comprise 2-100,000, 2-10,000, 2-5,000, 2-1,000, 2-500, 2-400, 2-300, 2-200, 2-100, 2-50, 2-20, 10-100,000, 10-10,000, 10-5,000, 10-1,000, 10-500, 10-400, 10-300, 10-200, 10-100, 10-50, 10-20, 50-100,000, 50-10,000, 50-5,000, 50-1,000, 50-500, 50-400, 50-300, 50-200, or 50-100 rAAV particles, nucleic acid vectors, or plasmids.

In some embodiments, the nucleic acid vector further comprises a heterologous nucleic acid region comprising a sequence encoding a protein or polypeptide of interest or an RNA of interest (such as a miRNA or siRNA or shRNA). In some embodiments, the heterologous nucleic acid region is contained within the intervening nucleic acid region between a first ITR and a second ITR. The protein or polypeptide of interest may be, e.g., a therapeutic protein, such as a human protein or an antibody, or a therapeutic polypeptide. Exemplary proteins or polypeptides of interest are provided in Table 2. The sequences of the polypeptide or protein of interest may be obtained, e.g., using the non-limiting National Center for Biotechnology Information (NCBI) Protein IDs or SEQ ID NOs from patent applications provided in Table 2. In some embodiments, the polypeptide or protein of interest is selected from the group consisting of FIX, FVIII, beta-catenin, beta-globin, pyruvate dehydrogenase, parvovirus B19 non-structural protein, and trichosanthin. Non-limiting, exemplary RNAs of interest include YAP1(Yes-associated protein 1)-siRNA and survivin siRNA.

TABLE 2

Exemplary Proteins and polypeptides of interest

| Protein or Polypeptide | Non-limiting Exemplary diseases, disorders, or phenotypes | Non-limiting NCBI Protein IDs or Patent SEQ ID NOs |
|---|---|---|
| beta-catenin (CTNNB1) | hepatocellular carcinoma | NP_001091679.1, NP_001091680.1, NP_001895.1 |
| pyruvate dehydrogenase (PDH) | hepatocellular carcinoma | NP_000275.1, NP_001166925.1, NP_001166926.1, NP_001166927.1, NP_000916.2, NP_001166939.1 |

TABLE 2-continued

Exemplary Proteins and polypeptides of interest

| Protein or Polypeptide | Non-limiting Exemplary diseases, disorders, or phenotypes | Non-limiting NCBI Protein IDs or Patent SEQ ID NOs |
| --- | --- | --- |
| parvovirus B19 non-structural protein (B19 NS1) | hepatocellular carcinoma | YP_004928144.1 |
| Trichosanthin (TCS) | hepatocellular carcinoma | XP_008243881.1 |
| beta-globin (HBB) | hemoglobinopathies | NP_000509.1 |
| acid alpha-glucosidase (GAA) | Pompe disease | NP_000143.2, NP_001073271.1, NP_001073272.1 |
| Methyl CpG binding protein 2 (MECP2) | Rett syndrome | NP_001104262.1, NP_004983.1 |
| Aromatic L-amino acid decarboxylase (AADC) | Parkinson's disease | NP_000781.1, NP_001076440.1, NP_001229815.1, NP_001229816.1, NP_001229817.1, NP_001229818.1, NP_001229819.1 |
| Glial cell-derived neurotrophic factor (GDNF) | Parkinson's disease | NP_000505.1, NP_001177397.1, NP_001177398.1, NP_001265027.1, NP_954701.1 |
| Cystic fibrosis transmembrane conductance regulator (CFTR) | Cystic fibrosis | NP_000483.3 |
| Tumor necrosis factor receptor fused to an antibody Fc (TNFR:Fc) | Arthritis, Rheumatoid arthritis | SEQ ID NO: 1 of WO2013025079 |
| HIV-1 gag-proΔrt (tgAAC09) | HIV infection | SEQ ID NOs: 1-5 of WO2006073496 |
| Sarcoglycan alpha, beta, gamma, delta, epsilon, or zeta (SGCA, SGCB, SGCG, SGCD, SGCE, or SGCZ) | Muscular dystrophy | SGCA NP_000014.1, NP_001129169.1 SGCB NP_000223.1 SGCG NP_000222.1 SGCD NP_000328.2, NP_001121681.1, NP_758447.1 SGCE NP_001092870.1, NP_001092871.1, NP_003910.1 SGCZ NP_631906.2 |
| Alpha-1-antitrypsin (AAT) | Hereditary emphysema or Alpha-1-antitrypsin deficiency | NP_000286.3, NP_001002235.1, NP_001002236.1, NP_001121172.1, NP_001121173.1, NP_001121174.1, NP_001121175.1, NP_001121176.1, NP_001121177.1, NP_001121178.1, NP_001121179.1 |
| Glutamate decarboxylase 1 (GAD 1) | Parkinson's disease | NP_000808.2, NP_038473.2 |
| Glutamate decarboxylase 2 (GAD2) | Parkinson's disease | NP_000809.1, NP_001127838.1 |
| Aspartoacylase (ASPA) | Canavan's disease | NP_000040.1, NP_001121557.1 |
| Nerve growth factor (NGF) | Alzheimer's disease | NP_002497.2 |
| Granulocyte-macrophage colonystimulating factory (GM-CSF) | Prostate cancer | NP_000749.2 |
| Cluster of Differentiation 86 (CD86 or B7-2) | Malignant melanoma | NP_001193853.1, NP_001193854.1, NP_008820.3, NP_787058.4, NP_795711.1 |

TABLE 2-continued

Exemplary Proteins and polypeptides of interest

| Protein or Polypeptide | Non-limiting Exemplary diseases, disorders, or phenotypes | Non-limiting NCBI Protein IDs or Patent SEQ ID NOs |
|---|---|---|
| Interleukin 12 (IL-12) | Malignant melanoma | NP_000873.2, NP_002178.2 |
| neuropeptide Y (NPY) | Parkinson's disease, epilepsy | NP_000896.1 |
| ATPase, Ca++ transporting, cardiac muscle, slow twitch 2 (SERCA2) | Chronic heart failure | NP_001672.1, NP_733765.1 |
| Dystrophin or Minidystrophin | Muscular dystrophy | NP_000100.2, NP_003997.1, NP_004000.1, NP_004001.1, NP_004002.2, NP_004003.1, NP_004004.1, NP_004005.1, NP_004006.1, NP_004007.1, NP_004008.1, NP_004009.1, NP_004010.1, NP_004011.2, NP_004012.1, NP_004013.1, NP_004014.1 |
| Ceroid lipofuscinosis neuronal 2 (CLN2) | Late infantile neuronal ceroidlipofuscinosis or Batten's disease | NP_000382.3 |
| Neurturin (NRTN) | Parkinson's disease | NP_004549.1 |
| N-acetylglucosaminidase, alpha (NAGLU) | Sanfilippo syndrome (MPSIIIB) | NP_000254.2 |
| Iduronidase, alpha-1 (IDUA) | MPSI-Hurler | NP_000194.2 |
| Iduronate 2-sulfatase (IDS) | MPSII-Hunter | NP_000193.1, NP_001160022.1, NP_006114.1 |
| Glucuronidase, beta (GUSB) | MPSVII-Sly | NP_000172.2, NP_001271219.1 |
| Hexosaminidase A, α polypeptide, also called beta-Hexosaminidase alpha (HEXA) | Tay-Sachs | NP_000511.2 |
| Hexosaminidase B, β polypeptide, also called beta-Hexosaminidase beta (HEXB) | Tay-Sachs | NP_000512.1, NP_001278933.1 |
| Retinal pigment epithelium-specific protein 65 kDa (RPE65) | Leber congenital amaurosis | NP_000320.1 |
| Factor IX (FIX) | Hemophilia B | NP_000124.1 |
| Adenine nucleotide translocator (ANT-1) | progressive external ophthalmoplegia | NP_001142.2 |
| ApaLI | mitochondrial heteroplasmy, myoclonic epilepsy with ragged red fibers (MERRF) or mitochondrial encephalomyopathy, lactic acidosis, and stroke-like episodes (MELAS) | YP_007161330.1 |
| NADH ubiquinone oxidoreductase subunit 4 (ND4) | Leber hereditary optic | YP_003024035.1 |
| very long-acyl-CoA dehydrogenase (VLCAD) | very long-chain acyl-CoA dehydrogenase (VLCAD) deficiency | NP_000009.1, NP_001029031.1, NP_001257376.1, NP_001257377.1 |
| short-chain acyl-CoA dehydrogenase (SCAD) | short-chain acyl-CoA dehydrogenase (SCAD) deficiency | NP_000008.1 |
| medium-chain acyl-CoA dehydrogenase (MCAD) | medium-chain acyl-CoA dehydrogenase (MCAD) deficiency | NP_000007.1, NP_001120800.1, NP_001272971.1, NP_001272972.1, NP_001272973.1 |

TABLE 2-continued

Exemplary Proteins and polypeptides of interest

| Protein or Polypeptide | Non-limiting Exemplary diseases, disorders, or phenotypes | Non-limiting NCBI Protein IDs or Patent SEQ ID NOs |
|---|---|---|
| Myotubularin 1 (MTM1) | X-linked myotubular myopathy | NP_000243.1 |
| Myophosphorylase (PYGM) | McArdle disease (glycogen storage disease type V, myophosphorylase deficiency) | NP_001158188.1, NP_005600.1 |
| Lipoprotein lipase (LPL) | LPL deficiency | NP_000228.1 |
| sFLT01 (VEGF/PlGF (placental growth factor) binding domain of human VEGFR1/Flt-1 (hVEGFR1) fused to the Fc portion of human IgG(1) through a polyglycine linker) | Age-related macular degeneration | SEQ ID NOs: 2, 8, 21, 23, or 25 of WO2009105669 |
| Glucocerebrosidase (GC) | Gaucher disease | NP_000148.2, NP_001005741.1, NP_001005742.1, NP_001165282.1, NP_001165283.1 |
| UDP glucuronosyltransferase 1 family, polypeptide A1 (UGT1A1) | Crigler-Najjar syndrome | NP_000454.1 |
| Glucose 6-phosphatase (G6Pase) | GSD-Ia | NP_000142.2, NP_001257326.1 |
| Ornithine carbamoyltransferase (OTC) | OTC deficiency | NP_000522.3 |
| Cystathionine-beta-synthase (CBS) | Homocystinuria | NP_000062.1, NP_001171479.1, NP_001171480.1 |
| Factor VIII (F8) | Haemophilia A | NP_000123.1, NP_063916.1 |
| Hemochromatosis (HFE) | Hemochromatosis | NP_000401.1, NP_620572.1, NP_620573.1, NP_620575.1, NP_620576.1, NP_620577.1, NP_620578.1, NP_620579.1, NP_620580.1 |
| Low density lipoprotein receptor (LDLR) | Phenylketonuria (PKU) | NP_000518.1, NP_001182727.1, NP_001182728.1, NP_001182729.1, NP_001182732.1 |
| Galactosidase, alpha (AGA) | Fabry disease | NP_000160.1 |
| Phenylalanine hydroxylase (PAH) | Hypercholesterolaemia or Phenylketonuria (PKU) | NP_000268.1 |
| Propionyl CoA carboxylase, alpha polypeptide (PCCA) | Propionic acidaemias | NP_000273.2, NP_001121164.1, NP_001171475.1 |
| myosin 7A (MYO7A) | Usher syndrome 1B | NP_000251.3, NP_001120651.2, NP_001120652.1 |

The polypeptides and proteins provided in Table 2 are known in the art for use in rAAV particles (see, e.g., Adeno-Associated Virus Vectors in Clinical Trials. Barrie J. Carter. Human Gene Therapy. May 2005, 16(5): 541-550. doi:10.1089/hum.2005.16.541. Published in Volume: 16 Issue 5: May 25, 2005; Neuropharmacology. 2013 June; 69:82-8. doi: 10.1016/j.neuropharm.2012.03.004. Epub 2012 Mar. 17.; Adeno-associated virus (AAV) gene therapy for neurological disease. Weinberg M S1, Samulski R J, McCown T J. Gene therapy for lysosomal storage disorders. Yew N S, Cheng S H. Pediatr Endocrinol Rev. 2013 November; 11 Suppl 1:99-109; Directed evolution of novel adeno-associated viruses for therapeutic gene delivery. Bartel M A, Weinstein J R, Schaffer D V. Gene Ther. 2012 June; 19(6): 694-700. doi: 10.1038/gt.2012.20. Epub 2012 Mar. 8; Therapeutic in vivo gene transfer for genetic disease using AAV: progress and challenges. Mingozzi F, High K A. Nat Rev Genet. 2011 May; 12(5):341-55. doi: 10.1038/nrg2988). In some embodiments, the polypeptide or protein of interest is a human protein or polypeptide. However, other proteins or polypeptides may be used.

In some embodiments, the viral capsid comprises a modified capsid protein (e.g., a mutant VP3 protein) comprising at least one mutation. In some embodiments, the viral capsid comprises a modified capsid protein (e.g., a mutant VP3 protein) comprising at least one mutation as described in Table 3. The mutation may be, e.g., a substitution of a tyrosine, lysine, serine, or threonine (such as a surface-exposed tyrosine, lysine, serine, or threonine), or combinations thereof. Exemplary mutations are known in the art (see, e.g., US Publication Numbers US20100104561, US20130203841, US20130216501, US20130310443, and US20140050701; PCT Publication Number WO2013173512A2; U.S. application Ser. No. 14/214,011; and PCT Application Number PCT/US2014/039015. Each of these publications and applications are incorporated herein by reference in their entirety and in particular with respect to the capsid mutations described therein).

TABLE 3

Exemplary Mutant Capsid Proteins

| Serotype | Exemplary Mutations (numbered with reference to the wild-type VP3 sequence for the serotype) |
|---|---|
| AAV1 | Y705F, Y731F, T492V |
| AAV2 | Y444F + Y500F + Y730F, |
|  | Y272F + Y444F + Y500F + Y730F + T491V, |
|  | Y252F + Y272F + Y444F + Y500F + Y704F + 7Y30F |
| AAV3 | Y705F + Y731F |
|  | S663V + T492V |
| AAV5 | Y719F |
| AAV6 | Y705F + Y731F |
|  | T492V |
| AAV8 | Y733F |
| AAV9 | Y731F | rAAV Particles and Methods of Producing rAAV Particles

Aspects of the disclosure relate to recombinant AAV (rAAV) particles. The rAAV particles have many uses, e.g., in methods and pharmaceutical compositions for treating a disease in a subject in need thereof (e.g., a subject having a disease involving reduced protein expression that may be treated with gene therapy), in rAAV particle-derived vaccines, for infecting cells to screen rAAV particles for a desired phenotype (e.g., upregulation of a protein or polypeptide of interest in the cell), or for infecting animals to screen for pharmacokinetics and/or therapeutic efficacy of an rAAV.

In some embodiments, recombinant rAAV particles comprise a nucleic acid vector. In some embodiments, the nucleic acid vector is a modified AAV genome. In some embodiments, the nucleic acid vector contains a construct comprising (a) one or more heterologous nucleic acid regions comprising a sequence encoding a protein or polypeptide of interest and (b) one or more (ITR) sequences (comprising one or more modifications as described herein) flanking the one or more heterologous nucleic acid regions. In some embodiments, the nucleic acid vector is encapsidated by a viral capsid. In some embodiments, the nucleic acid vector is single-stranded (e.g., a ssAAV). Non-limiting, exemplary plasmids containing ssAAV nucleic acid vectors include pAAV-hrGFP (available from AGILENT, Cat Number 240074). In some embodiments, a double-stranded nucleic acid vector may be, for example, a self-complimentary vector that contains a region of the nucleic acid vector that is complementary to another region of the nucleic acid vector, initiating the formation of the double-strandedness of the nucleic acid vector (e.g., a scAAV). Non-limiting, exemplary plasmids containing scAAV nucleic acid vectors include pdsAAV-CBAp-E.

Accordingly, in some embodiments, a rAAV particle comprises a viral capsid and a nucleic acid vector as described herein, which is encapsidated by the viral capsid. In some embodiments, the viral capsid comprises 60 capsid protein subunits comprising VP1, VP2 and VP3. In some embodiments, the VP1, VP2, and VP3 subunits are present in the capsid at a ratio of approximately 1:1:10, respectively. In some embodiments, the nucleic acid vector comprises (a) an intervening nucleic acid region (e.g., comprising one or more heterologous nucleic acid regions comprising a sequence encoding a protein or polypeptide of interest or an RNA of interest) and (b) one or more ITR sequences as described herein flanking the intervening nucleic acid region. In some embodiments, the intervening nucleic acid region comprises one or more of (a) a sequence encoding a protein or polypeptide of interest or an RNA of interest, (b) a stuffer sequence (e.g., a sequence used to increase to the length of the intervening sequence), (c) a promoter and/or enhancer, and/or (d) wild-type AAV genomic sequence. In some embodiments, the nucleic acid vector comprises a construct comprising (a) one or more heterologous nucleic acid regions comprising a sequence encoding a protein or polypeptide of interest, (b) one or more nucleic acid regions comprising a sequence that facilitates expression of the heterologous nucleic acid region (e.g., a promoter and/or enhancer), and (c) one or more ITR sequences as described herein. In some embodiments, the nucleic acid vector comprises one or more heterologous nucleic acid regions comprising a sequence encoding a protein or polypeptide of interest or RNA of interest, optionally operably linked to a promoter, wherein the one or more heterologous nucleic acid regions are flanked on each side with an ITR sequence as described herein. The ITR sequences to be modified as described herein can be derived from any AAV serotype (e.g., 1, 2, 3, 4, 5, 6, 7, 8, 9, 10) or can be derived from more than one serotype. In some embodiments, the ITR sequences to be modified are derived from AAV2. ITR sequences and plasmids containing ITR sequences are known in the art and commercially available (see, e.g., products and services available from Vector Biolabs, Philadelphia, Pa.; Cellbiolabs, San Diego, Calif.; Agilent Technologies, Santa Clara, Ca; and Addgene, Cambridge, Mass.; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci USA. 1996 Nov. 26; 93(24):14082-7; and Curtis A. Machida. Methods in Molecular Medicine™. Viral Vectors for Gene Therapy Methods and Protocols. 10.1385/1-59259-304-6:201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference).

Non-limiting, exemplary ITR sequences are as follows (exemplary D-sequences are underlined and bolded:

5'ITR:

(SEQ ID NO: 11)
5'-ttggccactccctctctgcgcgctcgctcgctcactgaggccgggcg accaaaggtcgcccgacgcccgggctttgcccgggcggcctcagtgagcg agcgagcgcgcagagagggagtggccaactccatcactaggggttcct-

3'

3'ITR:

(SEQ ID NO: 12)
5'-aggaaccccctagtgatggagttggccactccctctctgcgcgctcgc tcgctcactgaggccgggcgaccaaaggtcgcccgacgcccgggctttgc ccgggcggcctcagtgagcgagcgagcgcgcagagagggagtggcca a-3'

In some embodiments, the nucleic acid vector comprises one or more regions comprising a sequence that facilitates expression of the heterologous nucleic acid, e.g., expression control sequences operatively linked to the heterologous nucleic acid. Numerous such sequences are known in the art. Non-limiting examples of expression control sequences include promoters, insulators, silencers, response elements, introns, enhancers, initiation sites, termination signals, and poly(A) tails. Any combination of such control sequences is contemplated herein (e.g., a promoter and an enhancer). In some embodiments, one or more of these sequences may be in one or both ITRs and/or in the intervening region between the ITRS, as aspects of the disclosure are not limited in this respect.

To achieve appropriate expression levels of the protein or polypeptide of interest, any of a number of promoters suitable for use in the selected host cell may be employed. The promoter may be, for example, a constitutive promoter, tissue-specific promoter, inducible promoter, or a synthetic promoter. For example, constitutive promoters of different strengths can be used. A nucleic acid vector described herein may include one or more constitutive promoters, such as viral promoters or promoters from mammalian genes that are generally active in promoting transcription. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A and cytomegalovirus (CMV) promoters. Non-limiting examples of constitutive mammalian promoters include various housekeeping gene promoters, as exemplified by the β-actin promoter.

Inducible promoters and/or regulatory elements may also be contemplated for achieving appropriate expression levels of the protein or polypeptide of interest. Non-limiting examples of suitable inducible promoters include those from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline.

Tissue-specific promoters and/or regulatory elements are also contemplated herein. Non-limiting, exemplary tissue specific promoters include Parvovirus B19p6 promoter, human alpha-fetoprotein promoter, CD11c promoter, PSA promoter, and Telomerase promoter.

Synthetic promoters are also contemplated herein. A synthetic promoter may comprise, for example, regions of known promoters, regulatory elements, transcription factor binding sites, enhancer elements, repressor elements, and the like.

In some embodiments, a nucleic acid vector described herein may also contain a marker or reporter gene sequence, e.g., a sequence encoding a fluorescent protein.

The rAAV particle may be of any AAV serotype, including any modification, derivative or pseudotype (e.g., 1, 2, 3, 4, 5, 6, 7, 8, 9, or 10, or pseudotypes/derivatives/modifications thereof). Such AAV serotypes and derivatives/pseudotypes/modifications, and methods of producing such derivatives/pseudotypes/modifications are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan A1, Schaffer D V, Samulski R J.). In some embodiments, the rAAV particle is a pseudotyped rAAV particle. In some embodiments, the pseudotyped rAAV particle which comprises (a) a nucleic acid vector comprising AAV2 ITRs (comprising one or more modifications as described herein) and (b) a capsid comprised of capsid proteins derived from AAVx (e.g., AAV1, AAV3, AAV4, AAV5, AAV6, AAV7, AAV8, AAV9, or AAV10). Methods for producing and using pseudotyped rAAV particles are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001).

Methods of producing rAAV particles and nucleic acid vectors are also known in the art and commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, a plasmid containing the nucleic acid vector may be combined with one or more helper plasmids, e.g., that contain a rep gene (e.g., encoding Rep78, Rep68, Rep52 and Rep40) and a cap gene (encoding VP1, VP2, and VP3), and transfected into a producer cell line such that the rAAV particle can be packaged and subsequently purified.

In some embodiments, the one or more helper plasmids are a first helper plasmid comprising a rep gene and a cap gene and a second helper plasmid comprising a E1a gene, a E1b gene, a E4 gene, a E2a gene, and a VA gene. In some embodiments, the rep gene is a rep gene derived from AAV2 and the cap gene is derived from AAV9. Helper plasmids, and methods of making such plasmids, are known in the art and commercially available (see, e.g., pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, Pa.; Cellbiolabs, San Diego, Calif.; Agilent Technologies, Santa Clara, Ca; and Addgene, Cambridge, Mass.; pxx6; Grimm et al. (1998), Novel Tools for Production and Purification of Recombinant Adenoassociated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081.; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188).

An exemplary, non-limiting, rAAV particle production method is described next. One or more helper plasmids are produced or obtained, which comprise rep and cap ORFs for the desired AAV serotype or pseudotype and the adenoviral VA, E2A (DBP), and E4 genes under the transcriptional control of their native promoters. HEK293 cells (available from ATCC®) are transfected via CaPO$_4$-mediated transfection, lipids or polymeric molecules such as Polyethylenimine (PEI) with the helper plasmid(s) and a plasmid containing a nucleic acid vector described herein. The HEK293 cells are then incubated for at least 60 hours to allow for rAAV particle production. Alternatively, in another example Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs for the desired AAV serotype or pseudotype and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known the art or described herein, e.g., by iodixanol step gradient, CsCl gradient, chromatography, or polyethylene glycol (PEG) precipitation.

Plasmids and Kits

Other aspects of the disclosure relate to a plasmid comprising a first inverted terminal repeat (ITR) sequence comprising a glucocorticoid receptor responsive element and/or a second ITR sequence comprising a transcription factor binding site. In some embodiments, a plasmid comprises two ITRs, wherein only one ITR has a complete D-sequence (or a portion thereof sufficient to provide rAAV functions described herein). Such plasmids are useful, e.g., to produce the rAAV particles described herein. The plasmid may further comprise, e.g., a multiple cloning site, a promoter, an enhancer, and/or a heterologous nucleic acid region comprising a sequence encoding a protein or polypeptide of interest. The plasmid may additionally comprise, e.g., an origin of replication and/or a selection marker.

Yet other aspects of the disclosure relate to a kit, comprising a rAAV particle, composition, nucleic acid vector, or a plasmid as described herein. The kit may further comprise one or more containers for housing the rAAV particle or plasmid. The kit may further comprise instructions for use, such as in a method described herein. The kit may further comprise one or more helper plasmids.

Methods

Other aspects of the disclosure relate to a method of delivering a nucleic acid vector to a cell comprising contacting a cell with a rAAV particle as described herein.

In some embodiments, the cell is a mammalian cell, such as a human cell, non-human primate cell, rat cell, or mouse cell. In some embodiments, the cell is a liver, brain, heart or retina cell.

In some embodiments, the rAAV particle comprises the first inverted terminal repeat (ITR) sequence and the method further comprises contacting the cell with a glucocorticoid receptor (GR) activator. Non-limiting exemplary GR activators include dexamethasone and Ginsenoside RG1. Other non-limiting exemplary GR activators are known in the art. In some embodiments, the GR activator is dexamethasone.

The contacting may be in vivo, e.g., by administering to a subject or in vitro, e.g., by contacting the cell in a dish or well. The subject may be a human or other mammal, such as a non-human primate, mouse, or rat.

In some embodiments of any one of the methods provided herein, the rAAV particle is contained within a composition. In some embodiments, the composition comprises a pharmaceutically acceptable carrier. Non-limiting examples of pharmaceutically acceptable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, polyacrylic acids, lubricating agents (such as talc, magnesium stearate, and mineral oil), wetting agents, emulsifying agents, suspending agents, preserving agents (such as methyl-, ethyl-, and propyl-hydroxy-benzoates), pH adjusting agents (such as inorganic and organic acids and bases), sweetening agents, and flavoring agents. Other non-limiting examples of pharmaceutically acceptable carriers include saline (e.g., sterilized, pyrogen-free saline), saline buffers (e.g., citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers are particularly useful for delivery of rAAV particles to human subjects. Methods for making such formulations are well known and can be found in, for example, Remington: The Science and Practice of Pharmacy, 22nd edition, Pharmaceutical Press, 2012.

In some embodiments, a method described herein may further comprise administering a composition comprising a rAAV particle as described herein to a subject in need thereof. In some embodiments, the subject has or is suspected of having a disease that may be treated with gene therapy. Exemplary diseases include, but are not limited to, Hemophilia B, Hemophilia A, Hepatocellular carcinoma, Hepatoblastoma, β-thalassemia, and Sickle cell disease. Other exemplary diseases include, but are not limited to, cystic fibrosis, San Filippo syndrome, lipoprotein lipase deficiency, alpha-1 antitrypsin deficiency, arthritis, hereditary emphysema, Leber's congenital amaurosis, age-related macular degeneration, muscular dystrophy (duchenne, LGMD2d and 2c), Parkinson's disease, Canavan's disease, Batten's disease, Alzheimer's disease, metachromatic leukodystrophy, alpha-1 antitrypsin deficiency, lipoprotein lipase deficiency, heart failure, rheumatoid arthritis, amyotrophic lateral sclerosis (ALS), spinal muscular atrophy (SMA), ornithine transcarbamylase deficiency, epilepsy, Rett syndrome, lysosomal storage disorders of skeletal muscle or CNS, or Pompe disease. These diseases, associated symptoms and signs of the diseases, and methods of diagnosis of the diseases are known in the art and available to the skilled practitioner. Treatment methods involving rAAV particles are also known in the art (see, e.g., Adeno-Associated Virus Vectors in Clinical Trials. Barrie J. Carter. Human Gene Therapy. May 2005, 16(5): 541-550. doi: 10.1089/hum.2005.16.541. Published in Volume: 16 Issue 5: May 25, 2005; Neuropharmacology. 2013 June; 69:82-8. doi: 10.1016/j.neuropharm.2012.03.004. Epub 2012 Mar. 17.; Adeno-associated virus (AAV) gene therapy for neurological disease. Weinberg M S1, Samulski R J, McCown T J. Gene therapy for lysosomal storage disorders. Yew N S, Cheng S H. Pediatr Endocrinol Rev. 2013 November; 11 Suppl 1:99-109; Directed evolution of novel adeno-associated viruses for therapeutic gene delivery. Bartel M A, Weinstein J R, Schaffer D V. Gene Ther. 2012 June; 19(6): 694-700. doi: 10.1038/gt.2012.20. Epub 2012 Mar. 8; Therapeutic in vivo gene transfer for genetic disease using AAV: progress and challenges. Mingozzi F, High K A. Nat Rev Genet. 2011 May; 12(5):341-55. doi: 10.1038/nrg2988).

The compositions described above may be administered to a subject in any suitable formulation by any suitable method. The route of administration of the composition may be oral, parenteral, by inhalation or topical. The term parenteral as used herein includes intravenous, intraarterial, intraperitoneal, intramuscular, intradermal, intrathoracic, intrathecal, and subcutaneous administration. The compositions described above are typically administered to a subject in an effective amount, that is, an amount capable of producing a desirable result. The desirable result will depend upon the active agent being administered, the subject and the disease being treated. For example, an effective amount of rAAV particles may be an amount of the particles that are capable of transferring a heterologous nucleic acid to a host organ, tissue, or cell. As is known in the art, dosage for any one subject depends on many factors, including the subject's size, body surface area, age, the particular composition to be administered, the active ingredient(s) in the composition, time and route of administration, general health, and other drugs being administered concurrently.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1. Involvement of Glucocorticoid Receptor Signaling in AAV2 Vector-Mediated Transgene Expression Adeno-associated virus 2 (AAV2), a non-pathogenic human parvovirus, has gained attention as a potentially safe and efficient vector for gene therapy (3, 4, 17). Several groups have undertaken studies to delineate various steps in the life cycle of AAV2, including viral binding and entry (27, 35, 36), intracellular trafficking (6, 10, 11, 30, 41), nuclear transport (37, 43), and viral second-strand DNA synthesis (24, 26, 42, 46). The AAV2 genome is single-stranded (ss), and viral second-strand DNA synthesis has been demonstrated to be a rate-limiting step in vector-mediated transgene expression (7, 8). The development of self-complementary (sc) AAV2 vectors that bypass the requirement for viral second-strand DNA synthesis has circumvented this problem (20, 21, 38), and facilitated its use (1, 19). A wealth of information is available on ssAAV2-host cell interactions, but only a handful of reports have been described for that of scAAV2 (5, 13, 18).

Figure 1B:
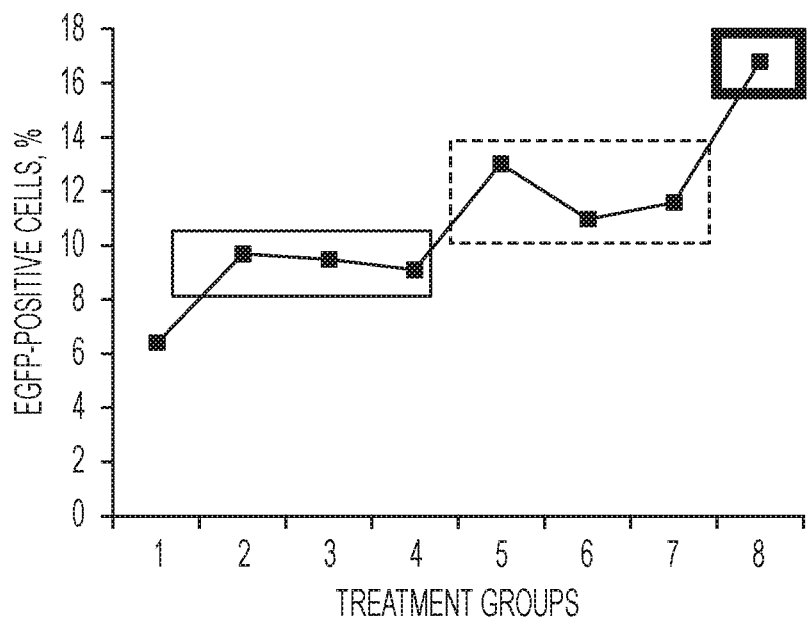
Figure 1C:
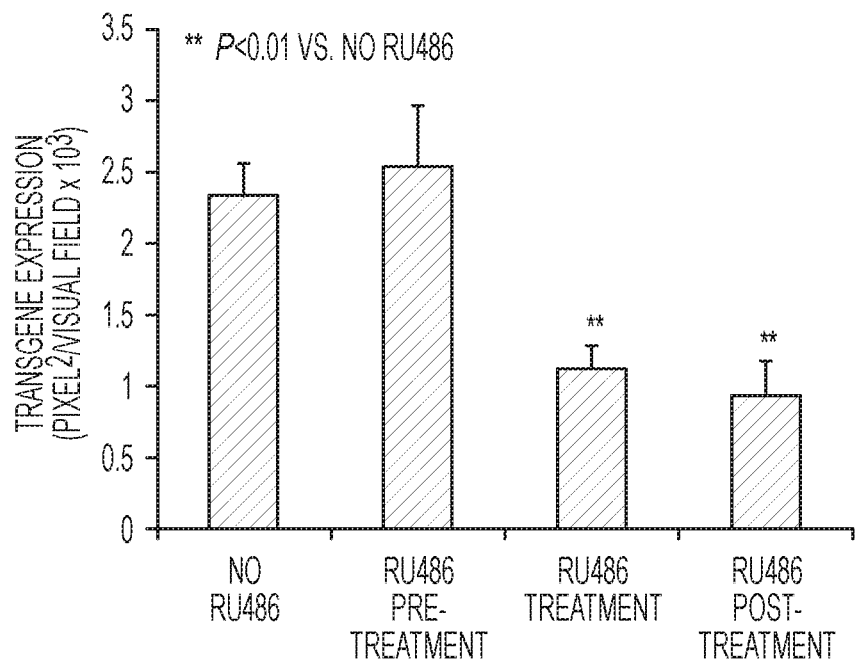
Figure 1D:
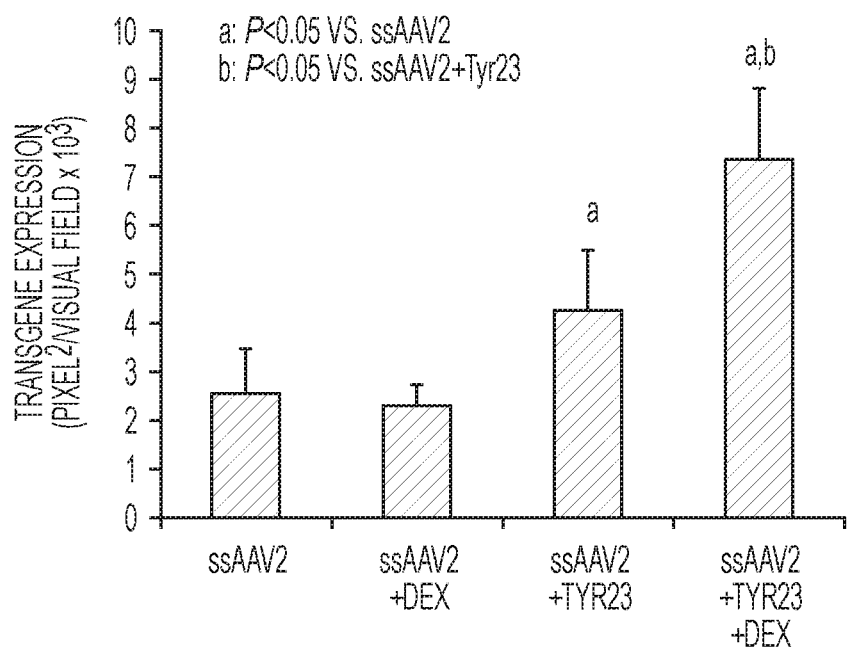

It was observed that infection by both ssAAV2 and scAAV2 vectors triggers activation of the NF-κB pathway (13). Since NF-κB activation is regulated by glucocorticoid receptor (GR) (31, 32), the present study undertook to evaluate whether AAV2 infection also involved GR signaling. The GR is present in its inactive hetero-complex form with cellular heat-shock protein 90 (HSP90), protein phosphatase 5 (PP5), and FK506-binding protein (FKBP51), and is activated by phosphorylation following ligand binding (2). Activated GR then undergoes immunophilin switching by substitution of FKBP51 with FKBP52, and enters the nuclear compartment through the FKBP52-dyenin network (39). Since it has been previously shown that HSP90 (44), FKBP52 (24, 25, 28), and PP5 (14, 15, 40) are involved in the AAV2 life cycle, the effect of dexamethasone (Dex), a GR activator (32), was evaluated on the transduction efficiency of both ssAAV2 and scAAV2 vectors. HeLa cells were treated for 12 hours with increasing concentrations of Dex prior to transduction with AAV2 vectors expressing enhanced green fluorescence protein (EGFP) driven by the chicken β-actin promoter (CBAp). These results are shown in FIG. 1. Up to an ~5-fold increase in transgene expression was achieved following Dex treatment by scAAV2 vectors (FIG. 1A), but not by ssAAV2 vectors (FIG. 1D), suggesting that GR activation is a positive regulator of scAAV2 vector-mediated transgene expression. In the next set of experiments, Dex was used at different stages, namely, treatment prior to infection, treatment during infection, and treatment post-infection. These results, shown in FIG. 1B, provide evidence that GR activation at any stage of infection facilitates scAAV2 vector-mediated transgene expression, and that sustained activation of GR yields the highest increase in transduction efficiency. To ascertain the specificity of Dex-mediated activation of GR, and its subsequent effect, a drug, RU486, known to inhibit GR activation by competing for the binding sites with its ligand, glucocorticoids (12) was used. HeLa cells were treated with RU486, and its effect on the transduction efficiency of scAAV2 vectors was evaluated as described above. As shown in FIG. 1C, RU486 treatment, but not pre-treatment, significantly reduced the transduction efficiency of scAAV2 vectors, suggesting that sustained GR activation may be required for increased transgene expression.

The puzzling lack of effect of Dex treatment on the transduction efficiency of ssAAV2 vectors was hypothesized to be related to the single-stranded nature of the viral genome. It was previously demonstrated that treatment of cells with Tyrphostin 23 (Tyr23), a specific inhibitor of cellular epidermal growth factor receptor protein tyrosine kinase (EGFR-PTK), facilitates viral second-strand DNA synthesis, and consequently, augments the transduction efficiency of ssAAV2 vectors (16, 45). HeLa cells were pre-treated with Tyr23, followed by transduction with ssAAV2 vectors, and incubated with and without Dex as described above. These results, shown in FIG. 1D, document that consistent with previously published studies (45), Tyr23 treatment significantly enhanced the transduction efficiency of ssAAV2 vectors, which was further augmented by Dex treatment. These data suggest that GR activation fails to affect ssAAV2 vector-mediated transgene expression unless the single-stranded viral genomes undergo second-stranded DNA synthesis.

Figure 2A:
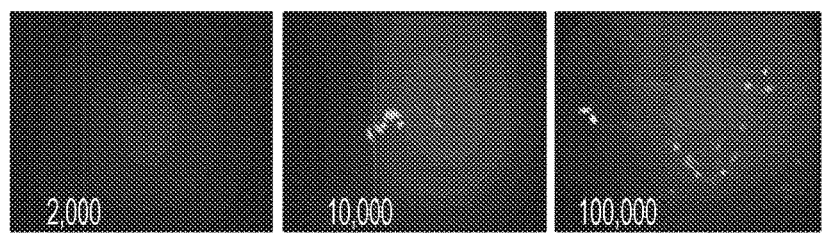
FIGS. 2A-C are a series of photographs and graphs.

To corroborate the contention that GR activation-mediated augmentation of the transduction efficiency of scAAV2 vectors is specific, a human osteosarcoma cell line, U2OS, which lacks endogenous GR expression (22) was used. It has previously been reported that U2OS cells are transduced extremely poorly by ssAAV2 vectors, even at very high multiplicities of infection (MOIs) (9). In the present studies, it was observed that very high MOIs were required for minimal transduction for U2OS cells by scAAV2 vectors as well. As shown in FIG. 2A, no EGFP signal was seen at an MOI of 2,000 vgs/cell, and only a limited number of green cells were seen at an MOI of 10,000 vgs/cell. Even at an MOI of 100,000 vgs/cells, only a modest level of transduction was observed. The low transduction efficiency in U2OS cells was not due to the lack of expression of heparan surface proteoglycan (HSPG), the primary receptor for AAV2 (36) (data not shown).

Figure 2B:
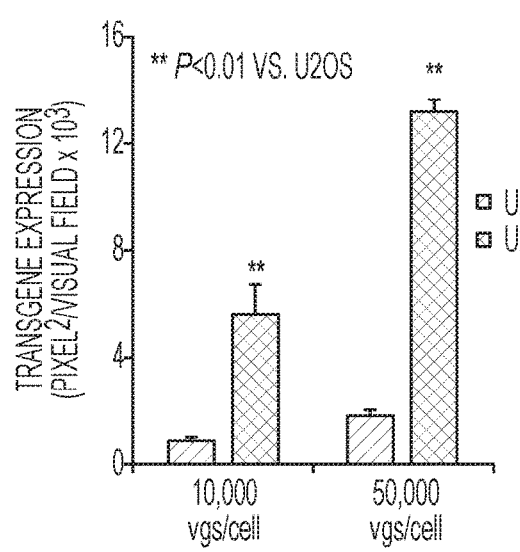
Figure 2C:
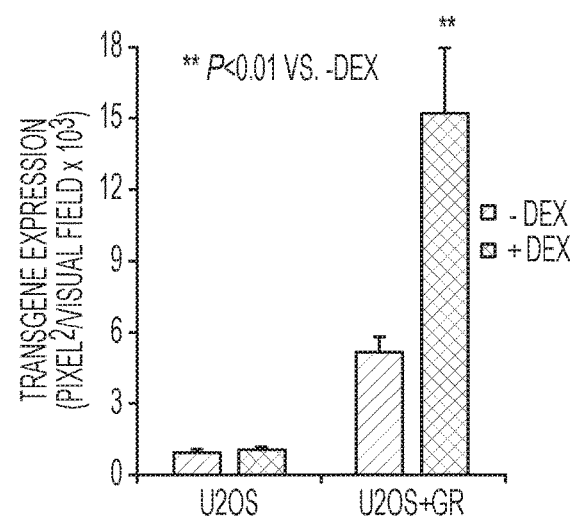

It was next examined as to whether re-introduction of GR into U2OS cells could restore the scAAV2 vector transduction efficiency. To this end, U2OS cells were stably transfected with a human GR expression plasmid, and the parental (U2OS) cells as well as those expressing GR (U2OS+GR) cells were transduced with scAAV2 vectors at MOIs of 10,000 and 50,000 vgs/cell. These results, shown in FIG. 2B, clearly show that the transduction efficiency of scAAV2 vectors was ~7-fold higher in U2OS+GR cells compared with the parental U2OS cells. Furthermore, whereas Dex-induced GR activation had no significant effect on vector-mediated transgene expression in the parental U2OS cells, the transduction efficiency of scAAV2 vectors in U2OS+GR cells was significantly increased following Dex treatment (FIG. 2C). Taken together, these results provide further evidence that GR signaling is involved in scAAV2 vector-mediated transgene expression.

Figure 3A:
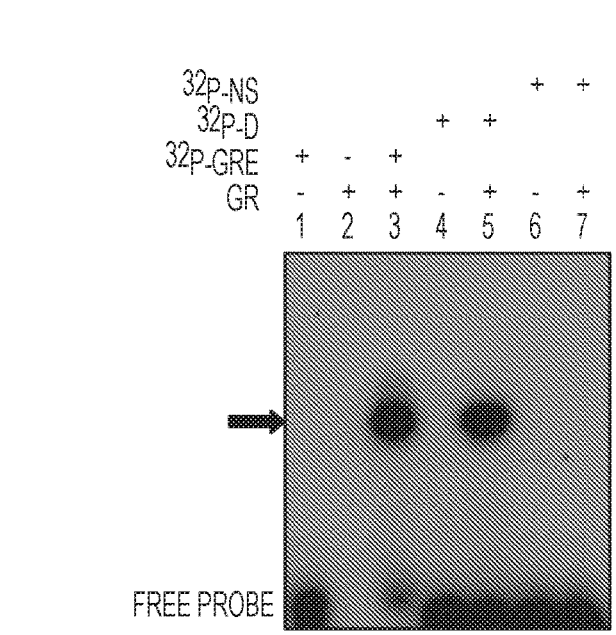
FIGS. 3A-B are a series of photographs.
Figure 3B:
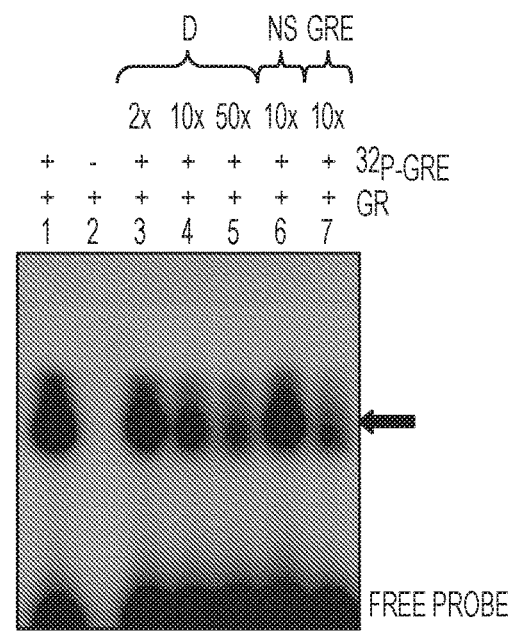

The classical model for GR function is based on the binding of a hormone-GR complex to the double-stranded GR response elements (GREs) in the regulatory regions of target genes, thereby changing the expression pattern of these genes (32). The recombinant AAV genomes contain inverted terminal repeats (ITRs) of 145 nucleotides at both ends (33). In ssAAV2 vector genomes, the terminal 125 nucleotides in each ITR form a palindromic double-stranded T-shaped hairpin structure, and the remaining 20 nucleotides, termed the D-sequence, remain single-stranded (33). In contrast, both D-sequences in the scAAV2 genomes are present in double-stranded forms. Since GR activation had no effect on the transduction efficiency for ssAAV2 vectors, it was hypothesized that the D-sequence might contain a putative GRE site. Indeed, there exists a sequence, GGTTCCT, at the end of the D-sequence, which shares partial homology to the consensus GRE site, 5'-GGTA-CANNNTGT(T/C)CT-3' (SEQ ID NO: 1) (34). The TGTTCT half-site is an essential core element which has been reported to be sufficient to relay glucocorticoid signaling (34). To experimentally test the possibility whether purified GR protein could bind to the D-sequence, electrophoretic mobility-shift assays (EMSAs) were carried out using double-stranded D-sequence oligonucleotides (D: 5'-CTCCATCACTAGGGGTTCCT-3') (SEQ ID NO: 6). One of the conventional double-stranded GRE sequences (GRE: 5'-CTAGGCTGTACAGGATGTTCTGCCTAG-3') (SEQ ID NO: 13), and a non-specific (NS) sequence (NS: 5'-TATTAGATCTGATGGCCGCT-3') (SEQ ID NO: 10) were used as appropriate positive and negative controls, respectively. Each of the $^{32}$P-labeled oligonucleotide probes was individually incubated with purified GR proteins for 20 minutes at 25° C. and then subjected to EMSAs. These results are shown in FIG. 3. Whereas the purified GR protein formed a specific complex with the GRE probe and retarded its mobility (FIG. 3A, lane 3), it also formed a similar complex with the D-sequence (FIG. 3A, lane 5), but not with the non-specific probe (FIG. 3A, lane 7). Densitometric scanning of autoradiographs revealed that the binding of GR to the conventional GRE probe was only slightly more efficient (compare lanes 3 and 5 in FIG. 3A) than that to the D-sequence probe. Correspondingly, the GR binding to the $^{32}$P-labeled GRE probe was competed with 2- to 50-fold molar excess of unlabeled D-sequence oligonucleotides (FIG. 3B, lanes 3-5), and with 10-fold molar excess of unlabeled GRE-sequence oligonucleotides (FIG. 3B, lane 7), but not with the unlabeled NS oligonucleotides (FIG. 3B, lanes 6). These data establish the specificity of the GR-D-sequence binding, and suggest that the D-sequence potentially functions as a half GRE site, forms a complex with the GR protein, and regulates scAAV2 vector-mediated transgene expression.

Although the presence of a GRE site in the mouse mammary tumor virus (MMTV) long terminal repeat (LTR), a retroviral promoter, and the hormonal activation of transcription from this promoter has been described (29), the significance of the presence of the half GRE site in the AAV2 genome is not readily apparent, given the transcriptionally inert nature of the viral genome. However, in view of the observation that AAV2 triggers activation of the NF-κB pathway (13), it stands to reason that AAV2 infection is also associated with GR activation, perhaps to dampen the host cell immune and inflammatory responses, known to be mediated by activation of the GR pathway. In this context, the use of Dex, in combination with bortezomib, a proteasome inhibitor, led to a significant reduction in humoral response to a transgene product in mice in vivo (23).

Figure 4A:
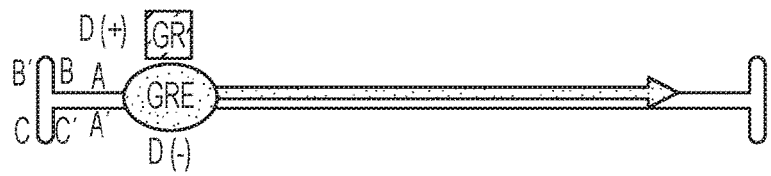
FIG. 4A shows the AAV2 genome with insertion of a full GRE site into the D sequence.

Next, it was hypothesized that engineering fully functional GRE sites in the D-sequence in the AAV2-ITRs, may exploit this feature to generate novel recombinant AAV vectors to achieve high-efficiency transgene expression as well as potentially dampened immune response. A full GRE site was cloned into the D(+)-sequence of the AAV2 genome, which also contained GFP as a marker (FIG. 4A). The full GRE set sequence was 5'-ggtacaggatgttct-3'. The GRE-containing AAV2 genomes were then packaged into wild-type AAV2 capsids (AAV2-GRE) or into mutant AAV2 capsids (Y444F+Y500+Y730F+T491V-GRE).

Figure 4B:
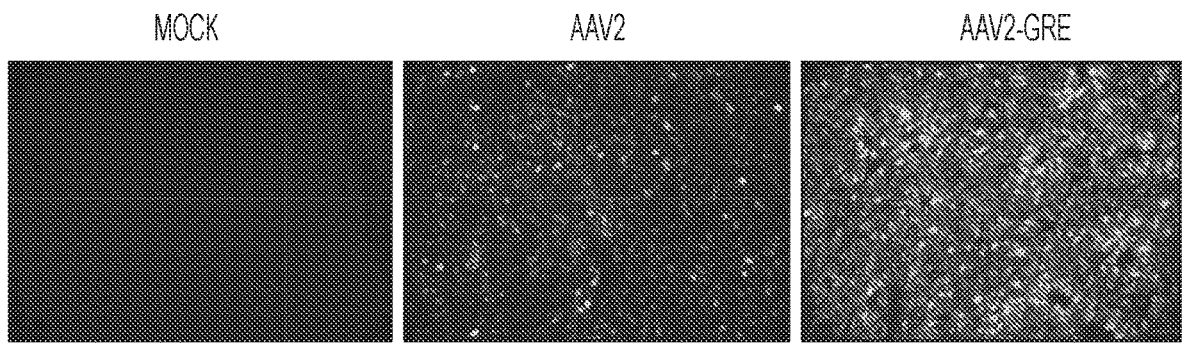
FIG. 4B shows a series of photographs of mouse hepatocytes transduced with mock, AAV2 or AAV2-GRE.
Figure 4C:
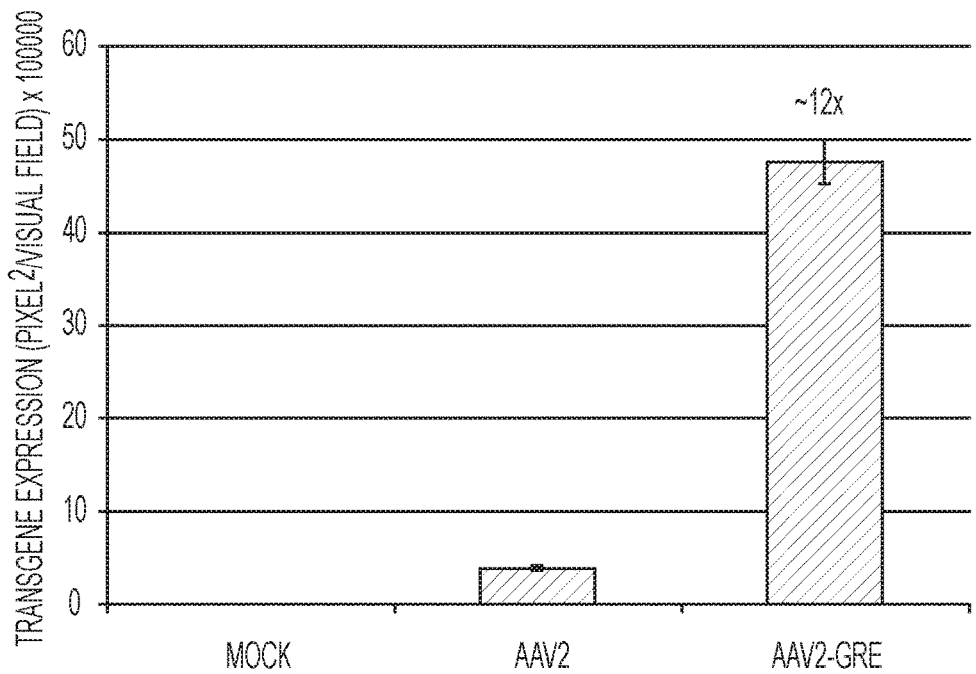
FIG. 4C shows a graph of transgene expression in mice treated with mock, AAV2, or AAV2-GRE.

Mice were injected with AAV2 or AAV2-GRE or with a mock control. $5 \times 10^{10}$ vgs were injected into each mouse. Eight weeks post-viral injection, half of the mice in each group were injected with dexamethasone at 0.2 mg/animal. Mouse sera were obtained at three time-points: 1) twenty four hours before dexamethasone injection, 2) six hours after, and 3) eighteen hours after dexamethasone injection. Transgene expression in the serum were then compared to determine the effect of dexamethasone in vivo. It was found that the in vivo GFP transgene expression AAV2-GRE was about 12 times higher than that of AAV2 (FIGS. 4B and C). Next, the AAV2 capsid-modified particles were tested.

Figure 5A:
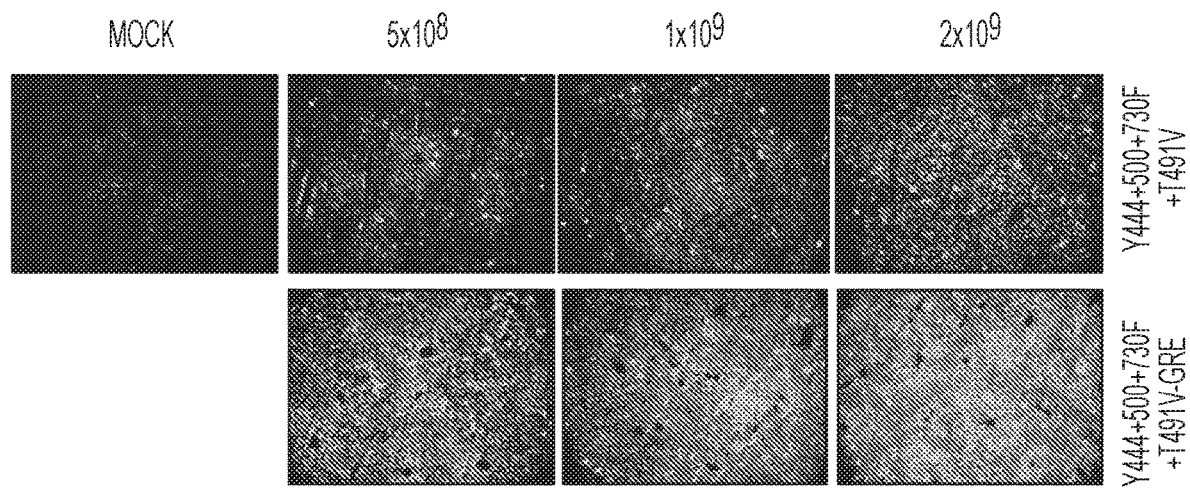
FIG. 5A shows a series of photographs of mouse hepatocytes transduced with mock, Y444+500+730F+T491V or Y444+500+730F+T491V-GRE.
Figure 5B:
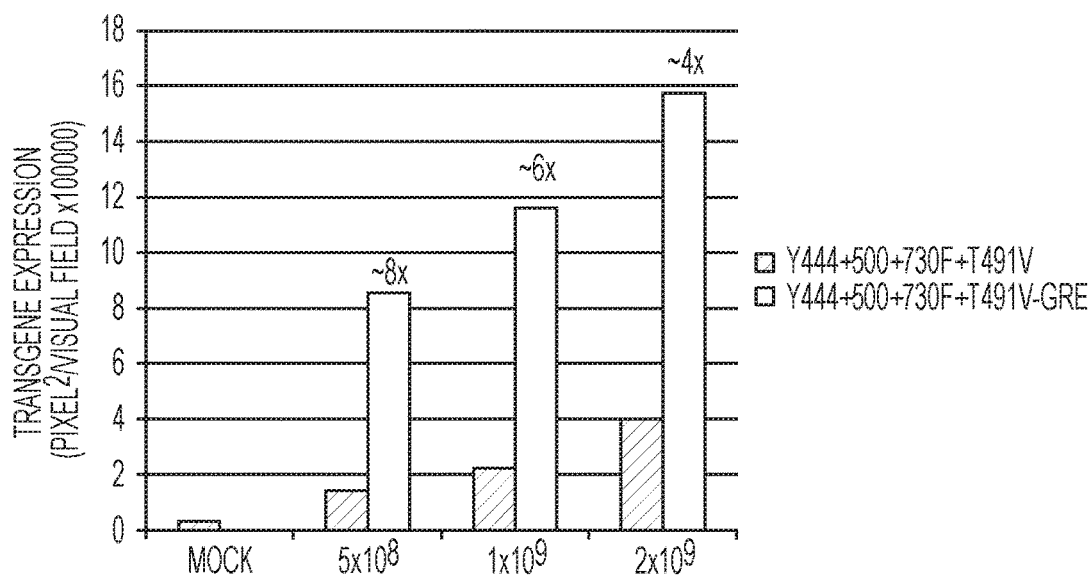
FIG. 5B shows a graph of transgene expression in mice treated with mock, Y444+500+730F+T491V or Y444+500+730F+T491V-GRE.

Mice were injected with Y444F+Y500+Y730F+T491V-GRE or Y444F+Y500+Y730F+T491V at $5 \times 10^8$, $1 \times 10^9$, or $2 \times 10^9$ vgs per mouse. It was found that the GRE containing particles had up to 8× more GFP transgene expression than the non-GRE containing particles (FIG. 5). These data show that the full GRE element-containing genomes had superior efficiency to wild-type genomes.

Lastly, mice were injected with scAAV2 vectors that contained either the half GRE site, a full GRE site, or a reversed GRE site. The viral vectors contained a Gaussia luciferase (GLuc) gene, the translated protein of which was secreted into blood. Eight weeks post-viral injection, mice sera was obtained and GLuc expression was determined. The results are shown in the table below. It was found that the full GRE site-containing scAAV2 vectors had the highest transduction efficiency.

| Group | Mouse ID | GLuc | Ave | SD |
|---|---|---|---|---|
| Mock | 6-N | 28.9 | 26.1 | 4.1 |
| | 7-N | 21.4 | | |
| | 8-N | 27.9 | | |
| scAAV2-GLuc | 6-L | 274.0 | 432.9 | 267.4 |
| | 7-L | 741.7 | | |
| | 8-L | 283.0 | | |
| scAAV2-Half GRE-GLuc | 6-R | 510.8 | 657.8 | 135.3 |
| | 7-R | 685.8 | | |
| | 8-R | 776.9 | | |
| scAAV2-Full GRE-GLuc | 6-LR | 3602.2 | 3063.3 | 590.6 |
| | 7-LR | 3155.7 | | |
| | 8-LR | 2431.9 | | |
| scAAV2-Reverse GRE-GLuc | 6-B | 571.3 | 518.7 | 46.2 |
| | 7-B | 485.0 | | |
| | 8-B | 499.8 | | |

REFERENCES FOR EXAMPLE 1

1. Beutler, A. S., and M. Reinhardt. 2009. AAV for pain: steps towards clinical translation. Gene Ther 16:461-9.
2. Bodwell, J. E., J. C. Webster, C. M. Jewell, J. A. Cidlowski, J. M. Hu, and A. Munck. 1998. Glucocorticoid receptor phosphorylation: overview, function and cell cycle-dependence. J Steroid Biochem Mol Biol 65:91-9.
3. Conlon, T. J., and T. R. Flotte. 2004. Recombinant adeno-associated virus vectors for gene therapy. Expert Opin Biol Ther 4:1093-101.
4. Daya, S., and K. I. Berns. 2008. Gene therapy using adeno-associated virus vectors. Clin Microbiol Rev 21:583-93.

5. Daya, S., N. Cortez, and K. I. Berns. 2009. Adeno-associated virus site-specific integration is mediated by proteins of the nonhomologous end joining pathway. J Virol 83:11655-64.
6. Douar, A. M., K. Poulard, D. Stockholm, and O. Danos. 2001. Intracellular trafficking of adeno-associated virus vectors: routing to the late endosomal compartment and proteasome degradation. J Virol 75:1824-33.
7. Ferrari, F. K., T. Samulski, T. Shenk, and R. J. Samulski. 1996. Second-strand synthesis is a rate-limiting step for efficient transduction by recombinant adeno-associated virus vectors. J Virol 70:3227-34.
8. Fisher, K. J., G. P. Gao, M. D. Weitzman, R. DeMatteo, J. F. Burda, and J. M. Wilson. 1996. Transduction with recombinant adeno-associated virus for gene therapy is limited by leading-strand synthesis. J Virol 70:520-32.
9. Fragkos, M., M. Breuleux, N. Clement, and P. Beard. 2008. Recombinant adeno-associated viral vectors are deficient in provoking a DNA damage response. J Virol 82:7379-87.
10. Hansen, J., K. Qing, H. J. Kwon, C. Mah, and A. Srivastava. 2000. Impaired intracellular trafficking of adeno-associated virus type 2 vectors limits efficient transduction of murine fibroblasts. J Virol 74:992-6.
11. Hansen, J., K. Qing, and A. Srivastava. 2001. Adeno-associated virus type 2-mediated gene transfer: altered endocytic processing enhances transduction efficiency in murine fibroblasts. J Virol 75:4080-90.
12. Honer, C., K. Nam, C. Fink, P. Marshall, G. Ksander, R. E. Chatelain, W. Cornell, R. Steele, R. Schweitzer, and C. Schumacher. 2003. Glucocorticoid receptor antagonism by cyproterone acetate and RU486. Mol Pharmacol 63:1012-20.
13. Jayandharan, G. R., G. Aslanidi, A. T. Martino, S. C. Jahn, G. Q. Perrin, R. W. Herzog, and A. Srivastava. 2011. Activation of the NF-kappaB pathway by adeno-associated virus (AAV) vectors and its implications in immune response and gene therapy. Proc Natl Acad Sci USA 108:3743-8.
14. Jayandharan, G. R., L. Zhong, B. Li, B. Kachniarz, and A. Srivastava. 2008. Strategies for improving the transduction efficiency of single-stranded adeno-associated virus vectors in vitro and in vivo. Gene Ther 15:1287-93.
15. Jayandharan, G. R., L. Zhong, B. K. Sack, A. E. Rivers, M. Li, B. Li, R. W. Herzog, and A. Srivastava. 2010. Optimized adeno-associated virus (AAV)-protein phosphatase-5 helper viruses for efficient liver transduction by single-stranded AAV vectors: therapeutic expression of factor IX at reduced vector doses. Hum Gene Ther 21:271-83.
16. Mah, C., K. Qing, B. Khuntirat, S. Ponnazhagan, X. S. Wang, D. M. Kube, M. C. Yoder, and A. Srivastava. 1998. Adeno-associated virus type 2-mediated gene transfer: role of epidermal growth factor receptor protein tyrosine kinase in transgene expression. J Virol 72:9835-43.
17. Marshall, E. 2001. Gene therapy. Viral vectors still pack surprises. Science 294:1640.
18. Martino, A. T., M. Suzuki, D. M. Markusic, I. Zolotukhin, R. C. Ryals, B. Moghimi, H. C. Ertl, D. A. Muruve, B. Lee, and R. W. Herzog. 2011. The genome of self-complementary adeno-associated viral vectors increases Toll-like receptor 9-dependent innate immune responses in the liver. Blood 117:6459-68.
19. McCarty, D. M. 2008. Self-complementary AAV vectors; advances and applications. Mol Ther 16:1648-56.
20. McCarty, D. M., H. Fu, P. E. Monahan, C. E. Toulson, P. Naik, and R. J. Samulski. 2003. Adeno-associated virus terminal repeat (TR) mutant generates self-complementary vectors to overcome the rate-limiting step to transduction in vivo. Gene Ther 10:2112-8.
21. McCarty, D. M., P. E. Monahan, and R. J. Samulski. 2001. Self-complementary recombinant adeno-associated virus (scAAV) vectors promote efficient transduction independently of DNA synthesis. Gene Ther 8:1248-54.
22. Meij sing, S. H., M. A. Pufall, A. Y. So, D. L. Bates, L. Chen, and K. R. Yamamoto. 2009. DNA binding site sequence directs glucocorticoid receptor structure and activity. Science 324:407-10.
23. Monahan, P. E., C. D. Lothrop, J. Sun, M. L. Hirsch, T. Kafri, B. Kantor, R. Sarkar, D. M. Tillson, J. R. Elia, and R. J. Samulski. 2010. Proteasome inhibitors enhance gene delivery by AAV virus vectors expressing large genomes in hemophilia mouse and dog models: a strategy for broad clinical application. Mol Ther 18:1907-16.
24. Qing, K., J. Hansen, K. A. Weigel-Kelley, M. Tan, S. Zhou, and A. Srivastava. 2001. Adeno-associated virus type 2-mediated gene transfer: role of cellular FKBP52 protein in transgene expression. J Virol 75:8968-76.
25. Qing, K., B. Khuntirat, C. Mah, D. M. Kube, X. S. Wang, S. Ponnazhagan, S. Zhou, V. J. Dwarki, M. C. Yoder, and A. Srivastava. 1998. Adeno-associated virus type 2-mediated gene transfer: correlation of tyrosine phosphorylation of the cellular single-stranded D sequence-binding protein with transgene expression in human cells in vitro and murine tissues in vivo. J Virol 72:1593-9.
26. Qing, K., W. Li, L. Zhong, M. Tan, J. Hansen, K. A. Weigel-Kelley, L. Chen, M. C. Yoder, and A. Srivastava. 2003. Adeno-associated virus type 2-mediated gene transfer: role of cellular T-cell protein tyrosine phosphatase in transgene expression in established cell lines in vitro and transgenic mice in vivo. J Virol 77:2741-6.
27. Qing, K., C. Mah, J. Hansen, S. Zhou, V. Dwarki, and A. Srivastava. 1999. Human fibroblast growth factor receptor 1 is a co-receptor for infection by adeno-associated virus 2. Nat Med 5:71-7.
28. Qing, K., X. S. Wang, D. M. Kube, S. Ponnazhagan, A. Bajpai, and A. Srivastava. 1997. Role of tyrosine phosphorylation of a cellular protein in adeno-associated virus 2-mediated transgene expression. Proc Natl Acad Sci USA 94:10879-84.
29. Ringold, G. M., K. R. Yamamoto, G. M. Tomkins, M. Bishop, and H. E. Varmus. 1975. Dexamethasone-mediated induction of mouse mammary tumor virus RNA: a system for studying glucocorticoid action. Cell 6:299-305.
30. Sanlioglu, S., P. K. Benson, J. Yang, E. M. Atkinson, T. Reynolds, and J. F. Engelhardt. 2000. Endocytosis and nuclear trafficking of adeno-associated virus type 2 are controlled by rac1 and phosphatidylinositol-3 kinase activation. J Virol 74:9184-96.
31. Scheinman, R. I., A. Gualberto, C. M. Jewell, J. A. Cidlowski, and A. S. Baldwin, Jr. 1995. Characterization of mechanisms involved in transrepression of NF-kappa B by activated glucocorticoid receptors. Mol Cell Biol 15:943-53.
32. Schoneveld, O. J., I. C. Gaemers, and W. H. Lamers. 2004. Mechanisms of glucocorticoid signalling. Biochim Biophys Acta 1680:114-28.
33. Srivastava, A., E. W. Lusby, and K. I. Berns. 1983. Nucleotide sequence and organization of the adeno-associated virus 2 genome. J Virol 45:555-64.
34. Strahle, U., G. Klock, and G. Schutz. 1987. A DNA sequence of 15 base pairs is sufficient to mediate both 35. Summerford, C., J. S. Bartlett, and R. J. Samulski. 1999. AlphaVbeta5 integrin: a co-receptor for adeno-associated virus type 2 infection. Nat Med 5:78-82.
36. Summerford, C., and R. J. Samulski. 1998. Membrane-associated heparan sulfate proteoglycan is a receptor for adeno-associated virus type 2 virions. J Virol 72:1438-45.
37. Thomas, C. E., T. A. Storm, Z. Huang, and M. A. Kay. 2004. Rapid uncoating of vector genomes is the key to efficient liver transduction with pseudotyped adeno-associated virus vectors. J Virol 78:3110-22.
38. Wang, Z., H. I. Ma, J. Li, L. Sun, J. Zhang, and X. Xiao. 2003. Rapid and highly efficient transduction by double-stranded adeno-associated virus vectors in vitro and in vivo. Gene Ther 10:2105-11.
39. Wochnik, G. M., J. Ruegg, G. A. Abel, U. Schmidt, F. Holsboer, and T. Rein. 2005. FK506-binding proteins 51 and 52 differentially regulate dynein interaction and nuclear translocation of the glucocorticoid receptor in mammalian cells. J Biol Chem 280:4609-16.
40. Zhao, W., J. Wu, L. Zhong, and A. Srivastava. 2007. Adeno-associated virus 2-mediated gene transfer: role of a cellular serine/threonine protein phosphatase in augmenting transduction efficiency. Gene Ther 14:545-50.
41. Zhao, W., L. Zhong, J. Wu, L. Chen, K. Qing, K. A. Weigel-Kelley, S. H. Larsen, W. Shou, K. H. Warrington, Jr., and A. Srivastava. 2006. Role of cellular FKBP52 protein in intracellular trafficking of recombinant adeno-associated virus 2 vectors. Virology 353:283-93.
42. Zhong, L., W. Li, Z. Yang, L. Chen, Y. Li, K. Qing, K. A. Weigel-Kelley, M. C. Yoder, W. Shou, and A. Srivastava. 2004. Improved transduction of primary murine hepatocytes by recombinant adeno-associated virus 2 vectors in vivo. Gene Ther 11:1165-9.
43. Zhong, L., W. Li, Z. Yang, K. Qing, M. Tan, J. Hansen, Y. Li, L. Chen, R. J. Chan, D. Bischof, N. Maina, K. A. Weigel-Kelley, W. Zhao, S. H. Larsen, M. C. Yoder, W. Shou, and A. Srivastava. 2004. Impaired nuclear transport and uncoating limit recombinant adeno-associated virus 2 vector-mediated transduction of primary murine hematopoietic cells. Hum Gene Ther 15:1207-18.
44. Zhong, L., K. Qing, Y. Si, L. Chen, M. Tan, and A. Srivastava. 2004. Heat-shock treatment-mediated increase in transduction by recombinant adeno-associated virus 2 vectors is independent of the cellular heat-shock protein 90. J Biol Chem 279:12714-23.
45. Zhong, L., W. Zhao, J. Wu, B. Li, S. Zolotukhin, L. Govindasamy, M. Agbandje-McKenna, and A. Srivastava. 2007. A dual role of EGFR protein tyrosine kinase signaling in ubiquitination of AAV2 capsids and viral second-strand DNA synthesis. Mol Ther 15:1323-30.
46. Zhong, L., X. Zhou, Y. Li, K. Qing, X. Xiao, R. J. Samulski, and A. Srivastava. 2008. Single-polarity recombinant adeno-associated virus 2 vector-mediated transgene expression in vitro and in vivo: mechanism of transduction. Mol Ther 16:290-5.

Example 2. Enhanced Transgene Expression from Recombinant Single-Stranded D-Sequence-Substituted Adeno-Associated Virus Vectors in Human Cell Lines In Vitro and in Murine Hepatocytes In Vivo The wild-type (WT) adeno-associated virus (AAV) is a non-pathogenic member of the Parvoviridae family with a 4.7 kb single-stranded (ss) DNA genome (1). It has gained particular attention because recombinant AAV (rAAV) vectors represent one of the most promising viral vector systems for gene therapy (2) and are currently in use in a number of gene therapy clinical trials (3). Most rAAV vectors used in clinical trials are single-stranded vectors. Viral second-strand DNA synthesis is one of the major rate limiting steps in ssAAV vector-mediated transgene expression (4-7). The development of self-complementary (sc) AAV vectors, which can bypass the requirement of viral second-strand DNA synthesis (8-10), has shown remarkable efficacy in the treatment of hemophilia B patients (11). However, a major limitation of scAAV vectors is their packaging capacity, which is ~2.5 kb. Such a limited packaging capacity excludes many larger therapeutic genes. When common promoters such as the cytomegalovirus (CMV) promoter and chicken beta-actin (CBA) promoter are used, a cDNA less than 1.2 kb can be packaged into the scAAV vectors. The inclusion of many tissue-specific promoters, such as the human alpha-1 antitrypsin (hAAT) promoter, further excludes many therapeutic genes, for instance the human Factor VIII gene (12). Therefore, strategies to improve the transduction efficiency of conventional ssAAV vectors are needed.

Both WT and rAAV genomes contain inverted terminal repeats (ITRs) of 145 nucleotides at both ends. The terminal 125 nucleotides in each ITR form a palindromic double-stranded T-shaped hairpin structure (1), in which the A-A' palindrome forms the stem, and the two smaller palindromes, B-B' and the C-C', form the cross-arms of the T. The other 20 nucleotides (D-sequence) in ITR remain single-stranded. The ssD[−] sequence is at the 3' end, whereas the complementary one, ssD[+] sequence is at the 5' end of the rAAV genome. Once in the cells, the single-stranded virus undergoes second-strand DNA synthesis, which turns both ssD[−] and ssD[+] sequence into double-stranded (ds) D[±] sequence. Phosphorylated forms of a 52-kDa cellular chaperone protein, FKBP52 (FK506-binding protein), specifically interact with ssD[−] sequence and hence inhibits viral second-strand DNA synthesis and subsequent transgene expression (7, 13-15). On the other hand, dephosphorylation of FKBP52 at tyrosine residues by the cellular T-cell protein tyrosine phosphatase (TC-PTP), and at serine/threonine residues by the protein phosphatase-5 (PP5), prevents FKBP52 from binding to the ssD[−] sequence, leading to efficient viral second-strand DNA synthesis (14, 16).

What role does the ssD[+] sequence play during the life cycle of AAV still remains unclear, although there exists a cellular protein which specifically interacts with the ssD[+]-sequence probe (6). Following purification and mass spectrometry, the cellular protein binding with the ssD[+] sequence was found to have partial amino acid homology to NF-κB repressing factor (NRF), a negative regulator of transcription (17). Since both the cellular proteins binding with either ssD[−] or ssD[+] sequence have the potential to inhibit transgene expression mediated by ssAAV vectors, and since the removal of the D-sequences from the viral genome impairs rescue, replication, and encapsidation of AAV DNA (18-20), it was examined as to whether restoration of one D-sequence in the ssAAV genome might not only restore rescue, replication, and encapsidation, but also enhance transgene expression from ssAAV vectors. It was shown that the ssD[+]-sequence-substituted ssAAV genomes could be successfully packaged into rAAV vectors, and that the transduction efficiency of these vectors was significantly higher than that of conventional ssAAV vectors.

Materials and Methods

Cell Lines, DNA Primers and $^{32}$P-Labeled Probes

Human cervical cancer (HeLa), embryonic kidney (HEK293), and osteosarcoma (U2OS) cells were purchased from American Type Culture Collection (Manassas, Va., USA). Human hepatocellular carcinoma (Huh7) cells were described previously (21). All cells were maintained in complete DMEM medium (C-DMEM, Mediatech Inc., Manassas, Va., USA) supplemented with 10% heat-inactivated fetal bovine serum (FBS, Sigma-Aldrich, St. Louis, Mo., USA), 1% penicillin and streptomycin (P/S, Lonza, Walkersville, Md.). Cells were grown as adherent culture in a humidified atmosphere at 37° C. in 5% CO2 and were sub-cultured after treatment with trypsin-versene mixture (Lonza, Walkersville, Md.) for 2-5 minutes at room temperature, washed and re-suspended in complete medium.

Primers-pairs, specific for CMVenhancer-F (5'-TCCCAT-AGTAACGCCAATAGG-3') (SEQ ID NO: 14) and CMVenhancer-R (5'-CTTGGCATATGATACACTTGATG-3') (SEQ ID NO: 15), were used in encapsidation assays. EcoR I- and Xho I-double digested or Xho I- and Rsr II-double digested plasmids pAAV-hrGFP, followed by gel recovery, were used as DNA templates to generate $^{32}$P-labeled hrGFP and hGH (A)n probes, respectively. Briefly, DNA templates were denatured by heating for 10 minutes at 100° C., followed by rapidly chilled in an ice bath. Random-primed labeling was performed using Klenow enzyme (Roche, Indianapolis, Ind., USA) following the manufacturer's instructions. $^{32}$P-labeled probes were then purified by Microspin™ G-50 Column (GE Healthcare, Piscataway, N.J., USA). To determine the polarity of the AAV vector genomes, two sets of identical slot blot membranes were hybridized separately with each one of the following two complementary oligonucleotides derived from the hrGFP, Probe hrGFP(+): 5'-GGG-GAAGCTCTGGA TGAAGAAGTCGCT-3' (SEQ ID NO: 16) and Probe hrGFP(−): 5'-AGCGACTTCTT-CATCCAGAGCTTCCCC-3'(SEQ ID NO: 17). The oligonucleotides were labeled prior to the hybridization using the DIG oligonucleotide 3'-end labeling kit (Roche, Indianapolis, Ind., USA) as per the manufacturer's instructions.

AAV DNA Rescue and Replication Assay

Equivalent amounts of each of the recombinant AAV plasmid were transfected in HEK293 cells together with pACG2 and pHelper by the triple-plasmid transfection protocol. At 72 hours post-transfection, low-Mr DNA samples were isolated using known methods (22) and digested extensively with Dpn I at 100 U/mL for 2 hours in a buffer containing 50 mM potassium acetate, 20 mM Tris-acetate, 10 mM magnesium acetate, and 1 mM DTT. Dpn I-treated samples were analyzed on Southern blots using $^{32}$P-labeled DNA probes specific for the hrGFP.

AAV DNA Encapsidation Assays

Equivalent amounts of each of the recombinant AAV plasmid were transfected together with pACG2 and pHelper by the triple-plasmid transfection protocol in HEK293 cells in 6-well plates. Cells were harvested 72 hours post-transfection, subjected to 3 rounds of freeze-thaw and then digested with 50 U/mL Benzonase (EMD Millipore, Darmstadt, Germany) at 37° C. for 1 hour. Cell lysate were then centrifuged at 4,000 rpm for 30 minutes. Equivalent amounts of supernatants were deproteinized to release the rAAV genome by incubation at 65° C. for 30 minutes in NaOH at a final concentration of 100 mM. The viral DNA was purified by DNA Clean & Concentrator-5 Kit (ZYMO Research, Irvine, Calif., USA) and subjected to qPCR assays.

Recombinant AAV Vectors

Highly purified stocks of AAV2 vectors, containing a CMV promoter driving the hrGFP expression gene, or containing a CBA promoter driving the firefly luciferase expression gene, were packaged by the triple-plasmid transfection protocol (23, 24). Briefly, HEK293 cells were co-transfected with three plasmids using polyethylenimine (PEI, linear, MW 25000, Polysciences, Inc., Warrington, Pa.), and medium was replaced 6 hours post-transfection. Cells were harvested 72 hours post-transfection, subjected to 3 rounds of freeze-thaw and then digested with 100 U/mL Benzonase (EMD Millipore, Darmstadt, Germany) at 37° C. for 1 hour. Viral vectors were purified by iodixanol (Sigma, St. Louis, Mo.) gradient ultra-centrifugation followed by ion exchange chromatography using HiTrap Q HP (GE Healthcare, Piscataway, N.J.), washed with PBS and concentrated by centrifugation using centrifugal spin concentrators with 150 K molecular-weight cutoff (MWCO). Viral vectors were resuspended in 500 μl PBS.

Quantitative DNA Slot Blot Analyses

The physical genomic titers of recombinant vector stocks were determined by quantitative DNA slot-blot as previously documented (25). Briefly, 10 μl vector stocks were digested with 100 U/mL Benzonase (EMD Millipore, Darmstadt, Germany) at 37° C. for 1 hour. An equal volume of 200 mM NaOH was added followed by incubation at 65° C. for 30 minutes. A known quantity of plasmid DNA was also treated in a same manner for use as a standard reference during quantitation. DNA samples were loaded in two-fold serial dilutions onto Immobilon-NY+TM membranes (Millipore, Bedford, Mass.). After cross-link, the membranes were then pre-hybridized for 6 hours at 68° C. in 25 mL hybridization solution containing 6×SSC, 100 μg/mL freshly-boiled herring sperm DNA, 0.5% sodium dodecyl sulfate (SDS), and 5×Denhardt's reagent. Subsequently, the membranes were hybridized with freshly-boiled $^{32}$P-labeled DNA probe in a total volume of 25 mL of hybridization solution at 68° C. for 18-20 hours. Membranes were then washed once in 50 mL wash solution 1 (2×SSC, 0.1% SDS) at room temperature (RT) for 15 minutes, twice in 50 mL wash solution 2 (0.1×SSC, 0.1% SDS) at 68° C. for 30 minutes, and then exposed to BIOMAX MR™ X-ray films (Kodak, Rochester, N.Y.) at −70° C.

Southern Blot Analyses

The viral DNA samples isolated from AAV DNA rescue and replication assays were purified by DNA Clean & Concentrator-5 Kit (ZYMO Research, Irvine, Calif., USA), dissolved in 20 μl ddH2O and electrophoresed on 1.2% native agarose gels. DNA was transferred to nylon membranes. Briefly, the gel was equilibrated at room temperature with solution I (0.25 M HCl) for 20 minutes, Solution II (1 M NaCl, 0.5 M NaOH) for 40 minutes, and Solution III (1 M NaCl, 0.5 M Tris-HCl) for 40 minutes. The DNA was transferred to Immobilon-NY+TM membranes (Millipore, Bedford, Mass.) in 20×SSC. After UV cross-linking, the membranes were treated as described above.

Western Blot Assay

Western blot assays were performed as previously described (26). Briefly, viral stocks were boiled for 10 minutes with loading buffer, separated using 12% SDS-PAGE electrophoresis, electro-transferred to nitrocellulose membranes (Bio-Rad), and probed with antibody B1 (ARP, Waltham, Mass., USA) at 4° C. overnight. The membranes were then incubated with horseradish peroxidase-conjugated secondary antibodies (1:5000 dilution, GE Healthcare, Piscataway, N.J., USA), and detected with an enhanced chemiluminescence substrate (MEMD Millipore, Billerica Mass., USA).

Recombinant AAV Vectors Transduction In Vitro

Cells were seeded in 96-well plates at 10,000 cells per well in C-DMEM. AAV infections were performed in serum- and antibiotic-free DMEM medium for 2 hours, followed by extensive washes with PBS to remove the vector inoculum. Transgene expression was analyzed by fluorescence microscopy 72 hours post-transduction. Alternatively, transgene expression was analyzed by flow cytometry 72 hours post-transduction.

Animal Handling

Six- to ten-weeks old C57BL/6J male mice were purchased from Jackson Laboratory (Bar Harbor, Me.). The Institutional Animal Care and Use Committee approved all protocols for the care and use of these mice.

Recombinant AAV Vector Transduction In Vivo

Recombinant ssAAV2 vectors were injected intravenously via tail vein into C57BL/6 mice at $1 \times 10^{10}$ vgs per animal. Phosphate-buffered saline (PBS)-injected mice were used as an appropriate control. For the fluorescence reporter gene, mice livers were harvested 2-, 4-, and 6-weeks post-vector administration, and thin sections from each hepatic lobe were mounted on slides and visualized under a fluorescence microscope. For the luciferase reporter gene, in vivo Fluc imaging was described previously (27). Briefly, mice were weighed to calculate the volume of substrate according to the dose of 4 mg/kg of body weight and anesthetized. The calculated volume of the 5 mg/mL of stock substrate solution was mixed with 100 µl of PBS and injected via intraperitoneal route. In vivo bioluminescence imaging were acquired immediately over a period of 5 minutes using a Xenogen machine equipped with a cooled couple-charged device camera (Xenogen, Alameda Calif.). Signal intensity was quantified using the camera control program, Living Image® software and shown as photons/second/cm$^2$/steridian (p/s/cm$^2$/sr).

Statistical Analysis

Results are presented as mean±standard deviation (SD). Differences between groups were identified using a grouped-unpaired two-tailed distribution of Student's T test. P values <0.05 were considered statistically significant.

Results

Figure 6A:
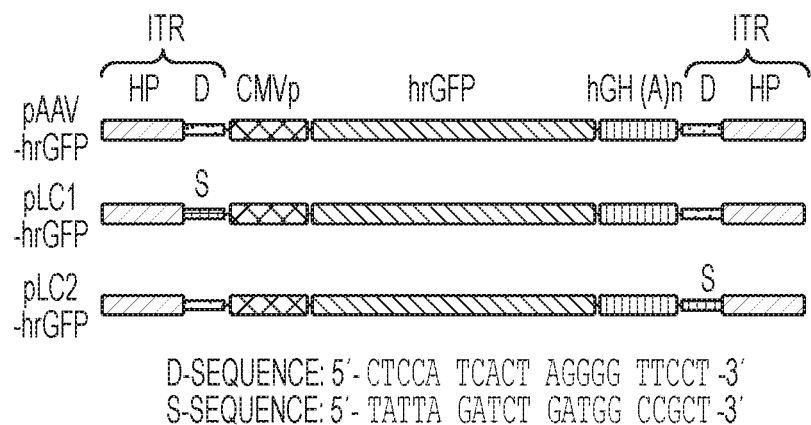
FIGS. 6A-D shows the effect of one D-sequence substitution on viral genome rescue and replication.

One D-Sequence Restores Rescue, Replication, and Encapsidation of Recombinant AAV Genomes To examine the consequences of substitution of the D-sequence in either ITR, the following two plasmids containing the identical expression cassette of a CMV promoter-driven humanized recombinant green fluorescent protein (hrGFP), flanked by two wild-type (WT) AAV2 ITRs of 145 nucleotides (FIG. 6A, top) were constructed: (i) pLC1-hrGFP, in which the D-sequence in the left ITR was substituted with a non-AAV substitute (S)-sequence (FIG. 6A, middle), and (ii) pLC2-hrGFP, in which the D-sequence in the right ITR was substituted with the S-sequence (FIG. 6A, bottom). The S-sequence was chosen due to the fact that this specific oligonucleotide does not interact with the cellular proteins that bind with the D-sequences (6), and that the S-sequence does not compete with the D-sequence (20). In addition, in each of the rAAV genomes, the terminal resolution sites (trs) in both ITRs remain functional (18-20), and the entire vector genome size is larger than 2.8 kb, which exceeds the packaging capacity of self-complementary (sc) AAV vectors (9, 10), to ensure that only virions containing ssAAV genomes were packaged (28-30).

Figure 6B:
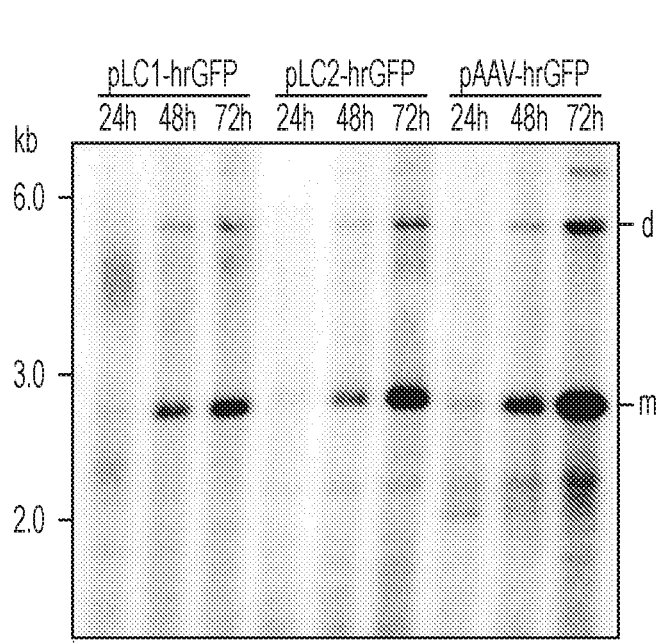

Recombinant AAV genome rescue and replication assays were performed following co-transfection of these plasmids separately into HEK293 cells with AAV (pACG2) and adenovirus-helper (pHelper) plasmids. Low-Mr DNA samples were isolated at various time points post-transfection, extensively digested with Dpn I, and analyzed on Southern blots using a $^{32}$P-labeled hrGFP-specific DNA probe. These results are shown in FIG. 6B. The kinetics of rAAV genome rescue and replication from both mutant plasmids pLC1-hrGFP and pLC2-hrGFP were nearly the same as that from pAAV-hrGFP, as determined by time-dependent accumulation of monomeric (m) and dimeric (d) forms of rAAV DNA replicative intermediates, albeit less efficiently. These results, nonetheless, suggest that the presence of one D-sequence in either of the two ITRs is necessary and sufficient for the rescue and replication of the rAAV genomes. These results further corroborate that the trs site in each of the D-sequence-substituted genomes was functional since both m and d forms of rAAV DNA replicative intermediates were detected, in contrast to the accumulation of only duplex DNA which occurs when scAAV vectors are used, which have a mutation in one trs (10).

The S-Sequence is Retained During AAV DNA Rescue and Replication

Figure 6C:
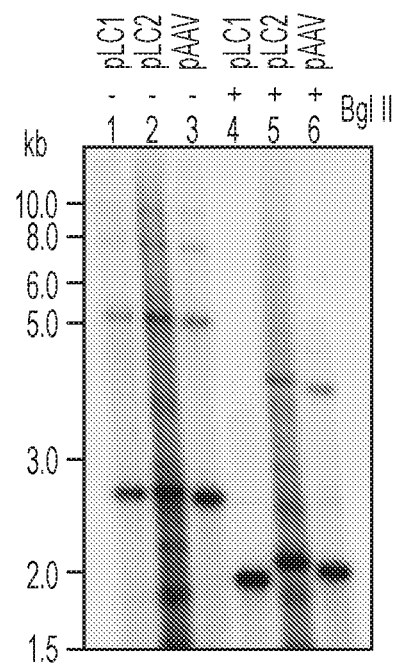

Since one ITR can serve as a template to repair the other ITR during AAV DNA rescue and replication (31), it was important to determine whether the D-sequence in one ITR displaced the S-sequence in the other ITR. To this end, low-Mr DNA samples isolated 72 hours post-transfection were digested with Dpn I, followed by digestion with or without Bgl II restriction endonuclease. The S-sequence contains an additional Bgl II site, and following digestion with Bgl II, the WT and the D-sequence-substituted AAV genomes would be expected to produce unique sets of restriction fragments that are consistent with the presence of both tail-to-tail (T-T) and head-to-head (H-H) configurations, provided that the S-sequence is not repaired. Southern blot analysis of Bgl II-digested DNA fragments using $^{32}$P-labeled probe specific for hrGFP produced the expected bands of 2.11 kb and 4.22 kb for pAAV-hrGFP (FIG. 6C, lane 6). Similarly, a 1.968 kb for pLC1 (FIG. 6C, lane 4), and two bands of 2.155 kb and 4.31 kb for pLC2 (FIG. 6C, lane 5) were also detected. These results demonstrate that the S-sequence in viral replicative DNA intermediates derived from pLC1 and pLC2 is not repaired during rescue and replication.

One D-Sequence Restores Encapsidation of the Mutant AAV Genomes

A standard triple-plasmid transfection protocol was used to generate rAAV vectors as described under Materials and Methods. Following digestion with Benzonase to degrade any unencapsidated DNA, equivalent volumes of virus stocks were deproteinized to release the rAAV genome and two-fold serial dilutions were analyzed on quantitative DNA slot blots using a $^{32}$P-labeled hrGFP DNA probe. These results, shown in FIG. 7A, demonstrate that the presence of one D-sequence in one of the two ITRs is necessary and sufficient for packaging of the AAV genome, albeit the vector titers appeared to be ~50% of those of the unmodified vectors presumably because progeny strands of only [+] or [−] polarity were being encapsidated. Similar results were obtained with multiple rounds (n=3 for each vector) of packaging of two different transgenes (data not shown). Analysis of the purified DNA on alkaline-agarose gels revealed the same ~2.8 kb genome from all three rAAV-hrGFP vectors, and no detectable linear monomers of 5.6 kb, indicating that scAAV vectors were not generated (FIG. 7B). Analysis of the denatured capsid proteins from purified viral stocks on SDS-Page gels, followed by Western blot analysis, also revealed a classic 1:1:10 ratio of VP1:VP2:VP3 proteins (FIG. 7C). In contrast to plasmid pAAV-hrGFP from which ssAAV vectors of both polarities were generated, as expected, the use of both mutant plasmids pLC1-hrGFP and pLC2-hrGFP led to the generation of predominantly only single-polarity vectors, as determined by using either [+] or [−] polarity hrGFP-specific oligonucleotide probes (FIG. 7D). For the most part, the hrGFP(+) probe hybridized to the minus-strand, whereas the hrGFP(−) probe hybridized to the plus-strand of the viral DNA. Thus, substitution of one D-sequence from one ITR leads to the generation of AAV vectors containing a single-polarity genome. Because the two vector genomes are complementary, these data suggest that AAV genomes containing the D[+]-sequence-substitution generated from both pLC1-hrGFP and pLC2-hrGFP plasmids undergo successful encapsidation.

One D-Sequence is Sufficient for Replication of Recombinant AAV Genomes

Figure 6D:
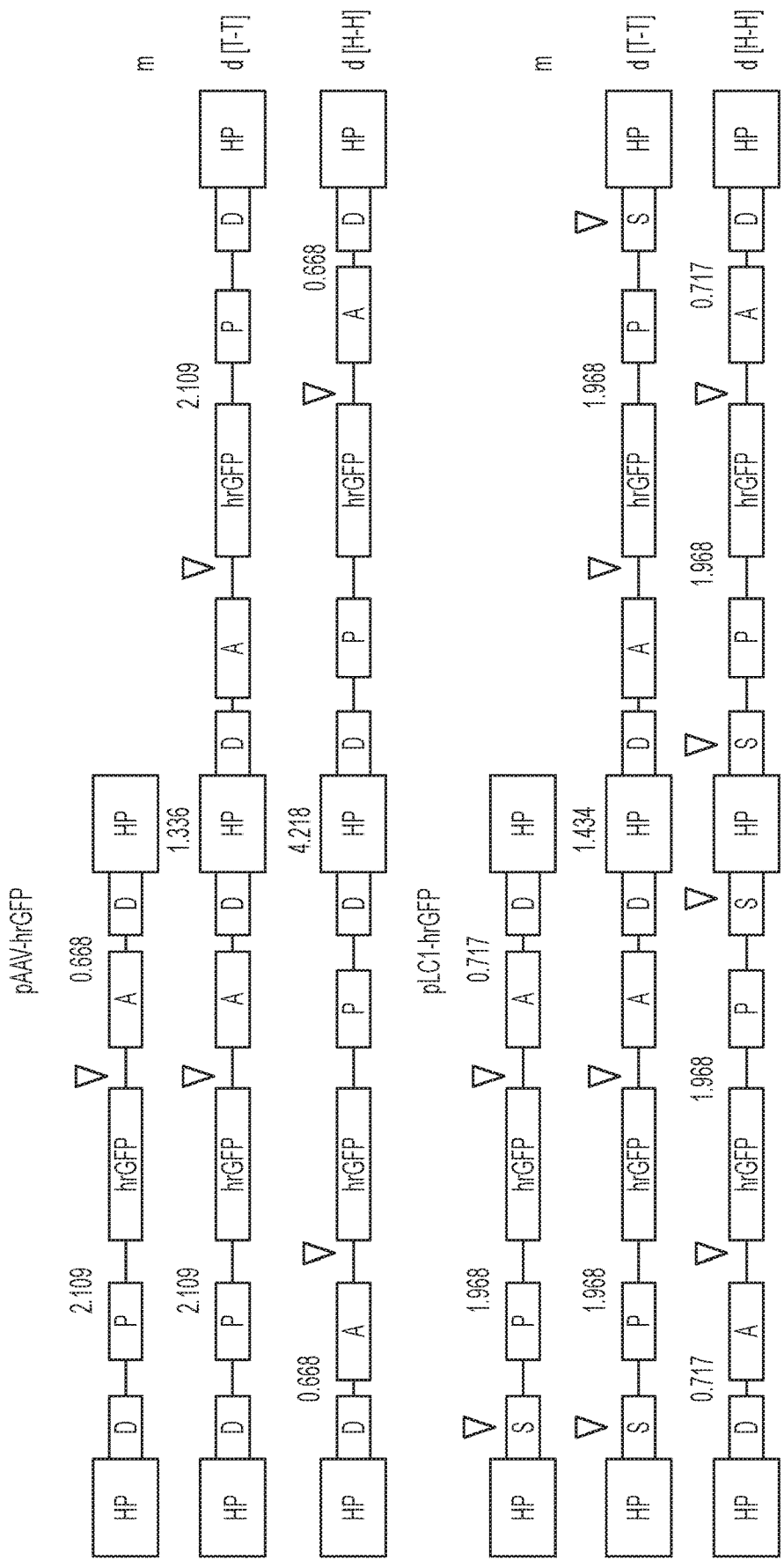
Figure 6D:
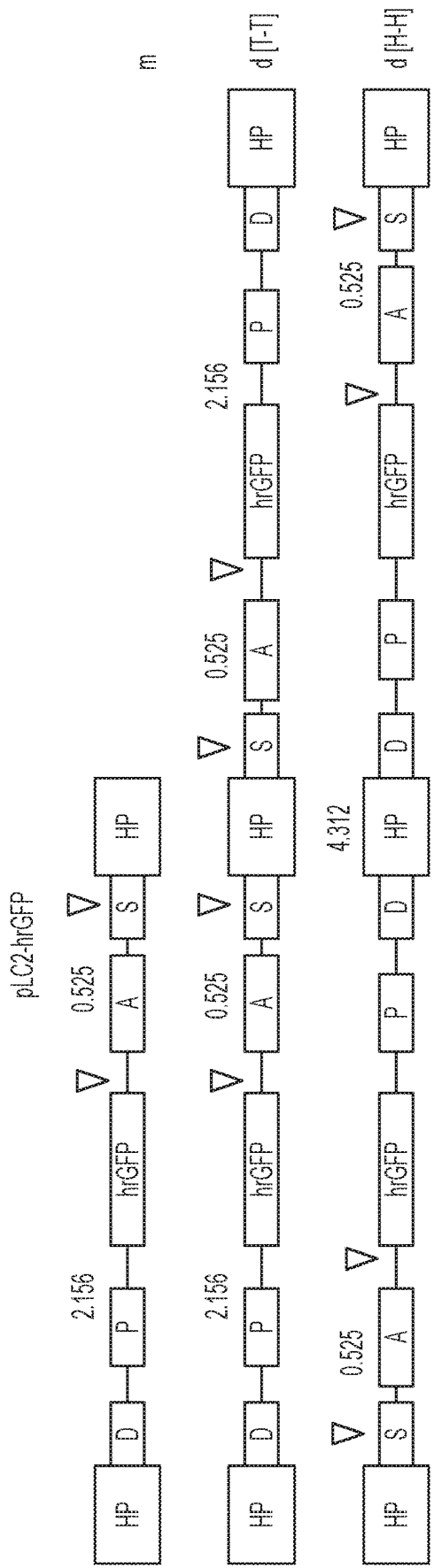
Figure 8:
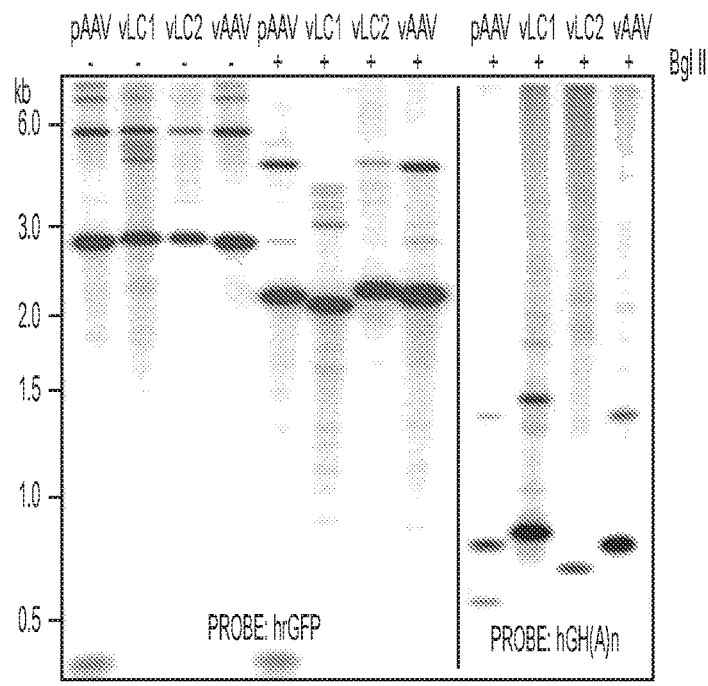
FIG. 8 shows southern blot analyses of replicative DNA intermediates containing substitutions in the D-sequence. HEK293 cells were infected with equal amount of vLC1-, vLC2- or vAAV-hrGFP virions and followed by transfection with plasmids pACG2 and pHelper. Low-Mr DNA was isolated 72 hours post-transfection, with or without Bgl II digestion. DNA was then separated by neutral agarose gel electrophoresis, followed by hybridization with $^{32}$P-labeled DNA probes, either specific for hrGFP (left panel) or for hGH(A)n (right panel).

HEK293 cells were infected with vAAV-hrGFP, vLC1-hrGFP, or vLC2-hrGFP vectors individually, followed by transfection with plasmids pHelper and pACG2. Plasmid pAAV-hrGFP was included as an appropriate control. The viral replication intermediates were isolated 72 hours post-infection, digested with Dpn I or/and Bgl II, and analyzed on Southern blots using $^{32}$P-labeled DNA probes specific for hrGFP or Poly A sequences, respectively. These results, shown in FIG. 8, indicated that both mutant viral genomes replicated at a similar level as the parental vAAV-hrGFP viral genomes. In addition, the presence of the expected DNA bands (FIG. 6D) in each corresponding group demonstrated that the S-sequence was retained during viral DNA replication.

Figure 9A:
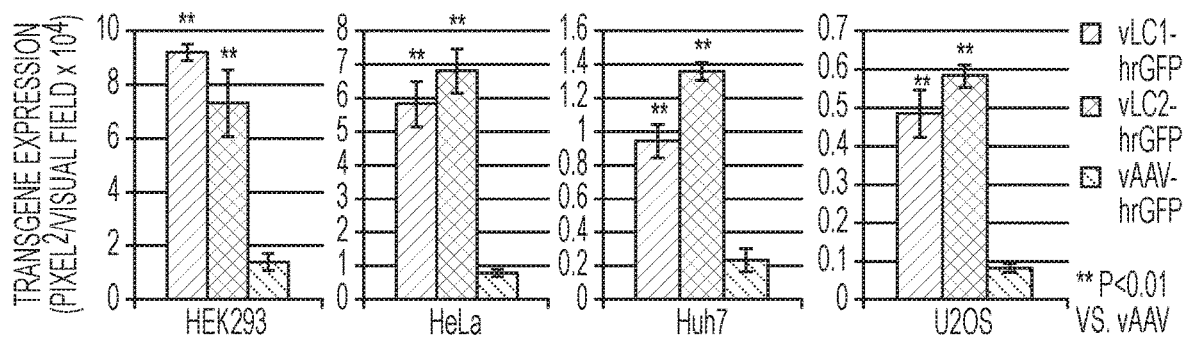
FIGS. 9A-G show transduction efficiency of one D-sequence-substituted recombinant AAV vectors in vitro.
Figure 9B:
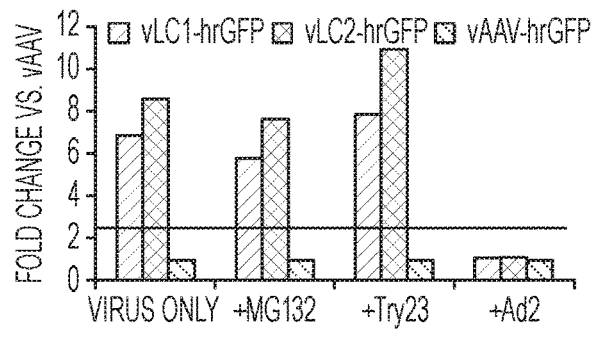
Figure 9C:
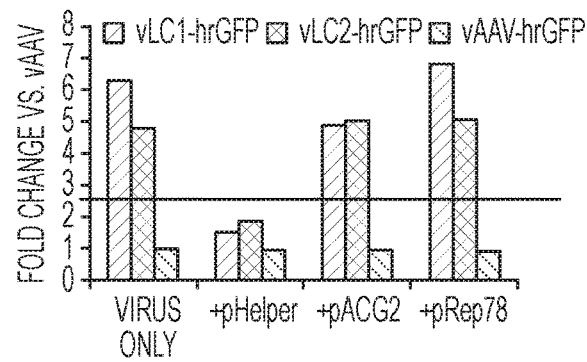
Figure 9D:
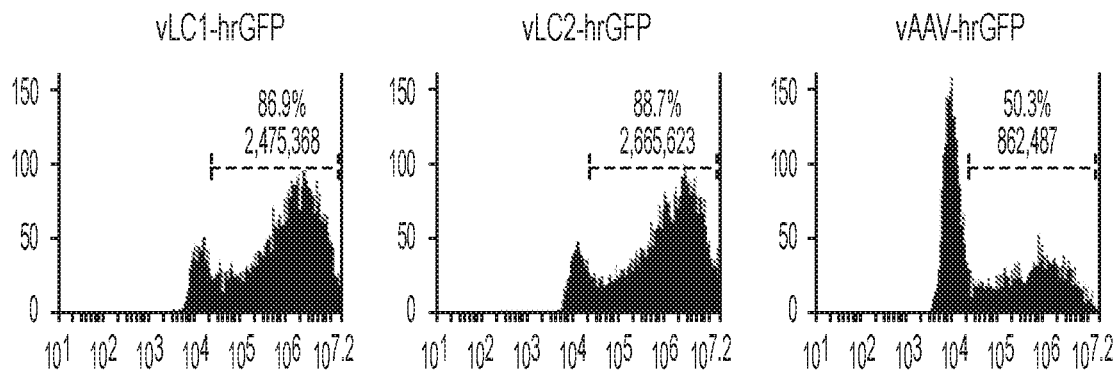
Figure 9E:
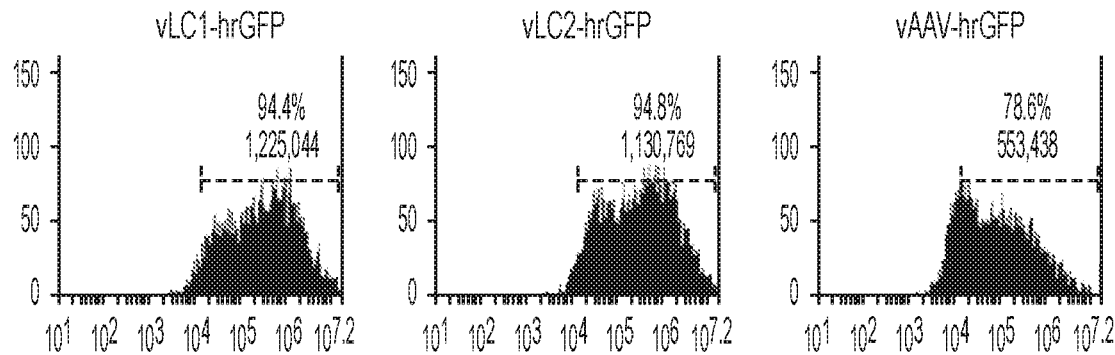
Figure 9F:
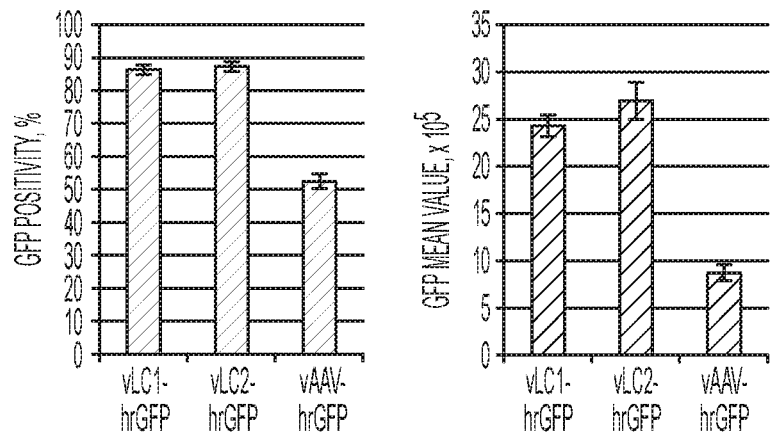
Figure 9G:
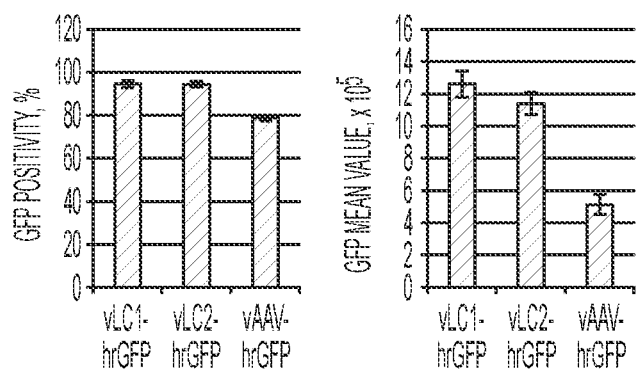

One D-Sequence-Substituted ssAAV2 Vectors Efficiently Transduce Human Cells In Vitro and Murine Hepatocytes In Vivo A panel of human cell lines was infected with each vector at 2,000 vgs/cell under identical conditions. The WT vAAV2-hrGFP vector was used as an appropriate control. As shown in FIG. 9A, in the commonly used HEK293 and HeLa cells, the mutant vectors, vLC1-hrGFP and vLC2-hrGFP, yielded ~8-fold more green fluorescence, compared with the WT vector. In Huh7 and U2OS, two cell lines less permissive for AAV2 vectors, we also observed ~6-fold increase in the transduction efficiency. The variation in transduction efficiencies was not affected when cells were pre-treated with MG132, a proteasome inhibitor, or Try23, a specific inhibitor of cellular EGFR protein kinase (FIG. 9B), both known to significantly increase the transduction efficiency of ssAAV2 vectors (13, 20), which indicates that neither intracellular trafficking nor proteasome degradation is involved. Co-infection with adenovirus type 2 (Ad2), led to similar levels of increase in transgene expression mediated by WT and the two mutant vectors in HEK293 cells (FIG. 9B), presumably because Ad2 co-infection is known to significantly increase the transduction efficiency of AAV vectors by augmenting the viral second-strand DNA synthesis, leading to optimal transgene expression (4, 5). HEK293 cells were transfected with plasmids pHelper, followed by infection with either mutant or parental viral vectors. The difference between increased transduction efficiencies was not significant (FIG. 9C). Two other plasmids, pACG2, which expresses AAV2 Rep and Cap proteins, and pRep78, which only expresses Rep 78, but no Cap proteins, had no effect. Flow cytometric analysis using both HeLa and 293 cells was performed. As can be seen in FIGS. 9D and 9E, both the GFP-positivity and the mean fluorescence values were increased in both vLC1-hrGFP- and vLC2-hrGFP-infected cells, compared with vAAV-hrGFP-infected cells.

Figure 10A:
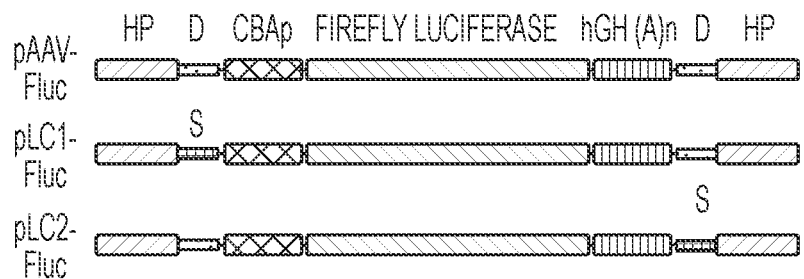
FIGS. 10A-C show transduction efficiency of one D-sequence-substituted recombinant AAV vectors in vivo.
Figure 10B:
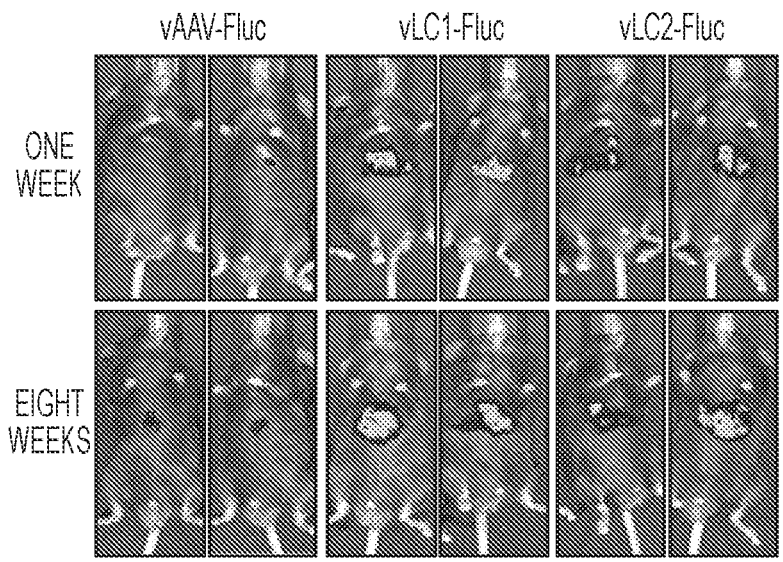
Figure 10C:
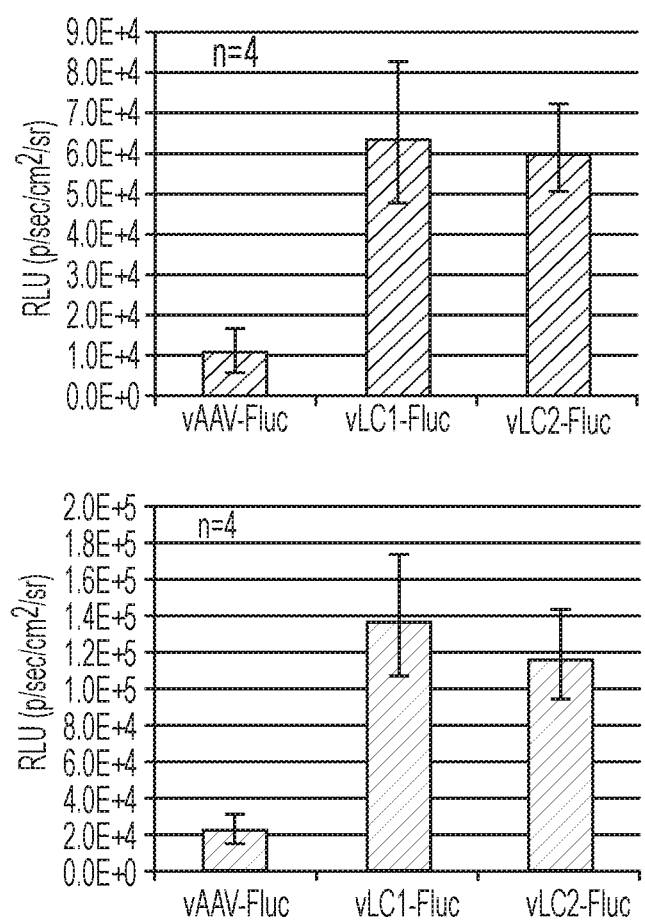

The efficacy of one D-sequence-substituted vLC2-hrGFP vector and the parental vAAV-hrGFP vectors was evaluated in a mouse model in vivo. C57BL/6J mice were injected via tail-vein with $1 \times 10^{10}$ vgs of each viral vector. Up to 6 weeks post-injection, vAAV-hrGFP transduction was slow and restricted to a small fraction of the hepatocytes. The transduction efficiency of vLC2 vectors was significantly higher even at two weeks (data not shown). To more accurately determine the transgene expression levels, persistence of expression, and anatomical localization of the delivered transgenes in individual animals over time, we generated recombinant WT- and D-sequence-substituted ssAAV2-Firefly luciferase (Fluc) vectors under the control of the chicken β-actin promoter (CBAp). The CBAp was used to avoid promoter shut-off, a known factor that CMV promoter in AAV vector is prone to in the liver (34). Approximately 1×1010 vgs of vAAV-Fluc, vLC1-Fluc, and vLC2-Fluc vectors (FIG. 10A) were injected via tail-vein in C57BL/6 mice. Whole-body bioluminescence images (FIG. 10B), acquired as detailed under Materials and Methods at either one- or eight-week post-injection, also corroborated that whereas little transgene expression occurred in mice injected with the WT vAAV-Fluc vectors, expression from both mutant vectors, vLC1-Fluc and vLC2-Fluc was up to 6-fold higher (FIG. 10C). These data demonstrate that the one D-sequence-substituted ssAAV vectors mediate accelerated and robust transgene expression than the conventional ssAAV vectors.

The unique structure of the 145 nts-long AAV-ITR has been intriguing since only the terminal 125 nts fold over to form a T-shaped hairpin, which at a first glance, would appear to suffice the priming of replication of the ssAAV genome, but the ITR also contains a stretch of 20 nts, designated as the D-sequence, which is single-stranded. Nearly two decades ago, several groups embarked upon the investigations to delineate the precise role of the D-sequence in the life cycle of WT AAV2, and documented that it plays a pivotal role in AAV genome rescue, replication, packaging, and integration (18-20). However, the fundamental question related to the underlying mechanisms of the involvement of the D-sequence in transgene expression from rAAV vectors remained unanswered. The subsequent realization that the two D-sequences in a rAAV genome were not identical, but in fact, complementary to each other, and that the ssD[−]-sequence was always present at the 3'-end, and the ssD[+]-sequence was invariably present at the 5'-end of the viral genome, prompted us to explore the possibility of the existence of putative host cell proteins which might interact with these sequences.

Indeed, using both ssD[−]- and ssD[+]-sequence probes in electrophoretic mobility-shift assays, two distinct cellular proteins were identified that formed specific complexes with the ssD[−]- and the ssD[+]-sequences, respectively (6). In an extensive set of experiments, the ssD[−]-sequence binding protein was identified (13), and the crucial role it plays in modulating the viral second-strand DNA synthesis was characterized (6, 7, 13-16, 35, 36). The identity of the ssD[+]-sequence binding protein was also revealed recently (17), as a negative regulator of transcription. These observations that proteins binding with the two D-sequences at each end of a viral genome are both involved in the inhibition of transgene expression led to the systematic studies described here. The experimental data shown in FIGS. 9 and 10, establish unequivocally that the substitution of one D-sequence partially relieves this negative regulation. In this context, it is important to note that in previously published studies (32, 33), in which 18 nts of the D-sequence were deleted, no increase in the transduction efficiency of these vectors was observed. In the current studies, not only the entire 20 nts D-sequence was deleted, but it was substituted with a non-AAV substitute (S)-sequence. Since improved transduction of these vectors was consistently observed in a number of human cell lines in vitro, as well as in murine hepatocytes in vivo, it was important to gain a better understanding for the observed differences from previously published studies. To this end, computational analyses were performed of both the D-sequence and the S-sequence using the following two databases available at: chip-mapper.org; and cbrc.jp/research/db/TFSEARCH.html (37, 38), which allowed for the identification of putative transcription factor binding sites in DNA genomes. These results revealed that the deletion of 18 nts from the D-sequence leads to the loss of putative binding sites for 2 transcription factors (Sry-delta, and Nkx2-1), whereas insertion of the S-sequence provided putative binding sites for 2 transcription factors (Foxd3, and NF-muE1). Thus, the net result is not only the loss of a negative regulator of transcription (NRF), but also the gain of 2 positive regulators of transcription in the D-sequence-substituted AAV vectors, which provides a plausible explanation as to why the vectors that have 18 nts deleted from the D-sequence do not show superior transduction, whereas the S-sequence-substituted AAV vectors do. A more stringent search, with a threshold score of 85, which provided a higher confidence value for binding of putative transcription factors revealed that the D-sequence contained the binding site for GATA-1, whereas the S-sequence contains binding sites for both GATA-1 and GATA-2 transcription factors. Thus, the loss of GATA-1 binding from the D-sequence-deleted AAV vectors, and the acquisition of GATA-1 and GATA-2 binding in the S-sequence-substituted AAV vectors provides yet another plausible explanation for the observed difference between previously published studies (32, 33), and those described here. It should be emphasized, however, that these explanations is based on theoretical computation only, and thus, additional studies involving the use of electrophoretic mobility-shift assays (EMSAs) may be warranted to further corroborate this contention.

Together, these observations raise an interesting existential question. Why, unlike all other DNA genome-containing organisms, does the WT AAV choose to remain single-stranded? One plausible answer is that in order to maintain its cryptic life cycle, AAV must exert enormous efforts to ensure that little viral gene expression occurs in the absence of a helper-virus. It is hypothesized that the WT AAV does so by employing a "dual safety-net". In the first instance, the D[−]-sequence is utilized to provide the binding site for a host cell protein, FKBP52, phosphorylated forms of which strongly inhibit the viral second-strand DNA synthesis (13) since the extent of viral DNA second-strand DNA synthesis correlates directly with the efficiency of viral gene expression. In the second stance, and in the event that some cell types that might allow even a low-level conversion to transcriptionally-active double-stranded viral genomes, AAV employs the D[+]-sequence to negatively regulate viral gene expression. How such a negative effect is rescued by the presence of adenoviral gene products, as shown in FIGS. 9B and 9C, may warrant further studies.

Given these built-in features, it would appear that the WT single-stranded AAV is less than ideal to be used as a recombinant vector for gene therapy to achieve high-level transgene expression. Initial attempts to develop rAAV vectors devoid of both of the D-sequences in one rAAV genome did not succeed, as these genomes failed to undergo encapsidation into rAAV capsids (18-20). In the present studies, however, in which only one of the two D-sequences was deleted in two respective plasmids, abundant rescue, followed by replication and encapsidation of the viral genomes ensued, albeit at ~50% efficiency because only single-polarity of the S-sequence-substituted progeny AAV genomes are generated and packaged, in contrast to their unmodified counterpart, which are known to generate and encapsidate progeny strands of both polarities that are packaged in mature particles with equal frequency.

In sum, the studies described here, in addition to providing insights into the basic biology of AAV, also provide a means to achieve augmented transgene expression from a conventional ssAAV vector by simply deleting the D-sequence in the right ITR. Given the fact that this strategy is also successful using AAV serotype 3 vectors (data not shown), it is believed that it should be applicable to any conventional ssAAV serotype vector. Furthermore, combining these strategies with recently described next generation of AAV vectors containing mutations in surface-exposed tyrosine, serine, and threonine residues (39-41), should further augment the transduction efficiency of all conventional ssAAV vectors for their potential use in human gene therapy.

REFERENCES FOR EXAMPLE 2

1. Srivastava A, Lusby E W, Berns K I. 1983. Nucleotide sequence and organization of the adeno-associated virus 2 genome. J Virol 45:555-564.
2. Ling C Q, Wang L N, Wang Y, Zhang Y H, Yin Z F, Wang M, Ling C. 2014. The roles of traditional Chinese medicine in gene therapy. J Integr Med 12:67-75.
3. Mingozzi F, High K A. 2011. Therapeutic in vivo gene transfer for genetic disease using AAV: progress and challenges. Nat Rev Genet 12:341-355.
4. Ferrari F K, Samulski T, Shenk T, Samulski R J. 1996. Second-strand synthesis is a rate-limiting step for efficient transduction by recombinant adeno-associated virus vectors. J Virol 70:3227-3234.
5. Fisher K J, Gao G P, Weitzman M D, DeMatteo R, Burda J F, Wilson J M. 1996. Transduction with recombinant adeno-associated virus for gene therapy is limited by leading-strand synthesis. J Virol 70:520-532.
6. Qing K, Wang X S, Kube D M, Ponnazhagan S, Bajpai A, Srivastava A. 1997. Role of tyrosine phosphorylation of a cellular protein in adeno-associated virus 2-mediated transgene expression. Proc Natl Acad Sci USA 94:10879-10884.
7. Zhong L, Chen L, Li Y, Qing K, Weigel-Kelley K A, Chan R J, Yoder M C, Srivastava A. 2004. Self-complementary adeno-associated virus 2 (AAV)-T cell protein tyrosine phosphatase vectors as helper viruses to improve transduction efficiency of conventional single-stranded AAV vectors in vitro and in vivo. Mol Ther 10:950-957.
8. McCarty D M, Monahan P E, Samulski R J. 2001. Self-complementary recombinant adeno-associated virus (scAAV) vectors promote efficient transduction independently of DNA synthesis. Gene Ther 8:1248-1254.
9. Wang Z, Ma H I, Li J, Sun L, Zhang J, Xiao X. 2003. Rapid and highly efficient transduction by double-stranded adeno-associated virus vectors in vitro and in vivo. Gene Ther 10:2105-2111.
10. McCarty D M, Fu H, Monahan P E, Toulson C E, Naik P, Samulski R J. 2003. Adeno-associated virus terminal repeat (T R) mutant generates self-complementary vectors to overcome the rate-limiting step to transduction in vivo. Gene Ther 10:2112-2118.
11. Nathwani A C, Tuddenham E G, Rangarajan S, Rosales C, McIntosh J, Linch D C, Chowdary P, Riddell A, Pie A J, Harrington C, O'Beirne J, Smith K, Pasi J, Glader B, Rustagi P, Ng C Y, Kay M A, Zhou J, Spence Y, Morton C L, Allay J, Coleman J, Sleep S, Cunningham J M, Srivastava D, Basner-Tschakarjan E, Mingozzi F, High K A, Gray J T, Reiss U M, Nienhuis A W, Davidoff A M. 2011. Adenovirus-associated virus vector-mediated gene transfer in hemophilia B. N Engl J Med 365:2357-2365.
12. Wu J, Zhao W, Zhong L, Han Z, Li B, Ma W, Weigel-Kelley K A, Warrington K H, Srivastava A. 2007. Self-complementary recombinant adeno-associated viral vectors: packaging capacity and the role of rep proteins in vector purity. Hum Gene Ther 18:171-182.
13. Qing K, Hansen J, Weigel-Kelley K A, Tan M, Zhou S, Srivastava A. 2001. Adeno-associated virus type 2-mediated gene transfer: role of cellular FKBP52 protein in transgene expression. J Virol 75:8968-8976.
14. Qing K, Li W, Zhong L, Tan M, Hansen J, Weigel-Kelley K A, Chen L, Yoder M C, Srivastava A. 2003. Adeno-associated virus type 2-mediated gene transfer: role of cellular T-cell protein tyrosine phosphatase in transgene expression in established cell lines in vitro and transgenic mice in vivo. J Virol 77:2741-2746.
15. Jayandharan G R, Zhong L, Sack B K, Rivers A E, Li M, Li B, Herzog R W, Srivastava A. 2009. Optimized adeno-associated virus (AAV)-protein phosphatase-5 helper viruses for efficient liver transduction by single-stranded AAV vectors: therapeutic expression of factor IX at reduced vector doses. Hum Gene Ther 21:271-283.
16. Zhao W, Wu J, Zhong L, Srivastava A. 2007. Adeno-associated virus 2-mediated gene transfer: role of a cellular serine/threonine protein phosphatase in augmenting transduction efficiency. Gene Ther 14:545-550.
17. Jayandharan G R, Aslanidi G, Martino A T, Jahn S C, Perrin G Q, Herzog R W, Srivastava A. 2011. Activation of the N F-kappaB pathway by adeno-associated virus (AAV) vectors and its implications in immune response and gene therapy. Proc Natl Acad Sci USA 108:3743-3748.
18. Wang X S, Ponnazhagan S, Srivastava A. 1995. Rescue and replication signals of the adeno-associated virus 2 genome. J Mol Biol 250:573-580.
19. Wang X S, Ponnazhagan S, Srivastava A. 1996. Rescue and replication of adeno-associated virus type 2 as well as vector DNA sequences from recombinant plasmids containing deletions in the viral inverted terminal repeats: selective encapsidation of viral genomes in progeny virions. J Virol 70:1668-1677.
20. Wang X S, Qing K, Ponnazhagan S, Srivastava A. 1997. Adeno-associated virus type 2 DNA replication in vivo: mutation analyses of the D sequence in viral inverted terminal repeats. J Virol 71:3077-3082.
21. Ling C, Lu Y, Kalsi J K, Jayandharan G R, Li B, Ma W, Cheng B, Gee S W, McGoogan K E, Govindasamy L, Zhong L, Agbandje-McKenna M, Srivastava A. 2010. Human hepatocyte growth factor receptor is a cellular coreceptor for adeno-associated virus serotype 3. Hum Gene Ther 21:1741-1747.
22. Hirt B. 1967. Selective extraction of polyoma DNA from infected mouse cell cultures. J Mol Biol 26:365-369.
23. Wang L N, Wang Y, Lu Y, Yin Z F, Zhang Y H, Aslanidi G V, Srivastava A, Ling C Q, Ling C. 2014. Pristimerin enhances recombinant adeno-associated virus vector-mediated transgene expression in human cell lines in vitro and murine hepatocytes in vivo. J Integr Med 12:20-34.
24. Liu Y, Joo K I, Wang P. 2013. Endocytic processing of adeno-associated virus type 8 vectors for transduction of target cells. Gene Ther 20:308-317.
25. Ling C, Lu Y, Cheng B, McGoogan K E, Gee S W, Ma W, Li B, Aslanidi G V, Srivastava A. 2011. High-efficiency transduction of liver cancer cells by recombinant adeno-associated virus serotype 3 vectors. J Vis Exp.
26. Dai Y, Bae K, Siemann D W. 2011. Impact of hypoxia on the metastatic potential of human prostate cancer cells. Int J Radiat Oncol Biol Phys 81:521-528.
27. Gu Y, Lin S, Li J L, Nakagawa H, Chen Z, Jin B, Tian L, Ucar D A, Shen H, Lu J, Hochwald S N, Kaye F J, Wu L. 2012. Altered LKB1/CREB-regulated transcription co-activator (CRTC) signaling axis promotes esophageal cancer cell migration and invasion. Oncogene 31:469-479.
28. Dong B, Nakai H, Xiao W. 2010. Characterization of genome integrity for oversized recombinant AAV vector. Mol Ther 18:87-92.
29. Wu Z, Yang H, Colosi P. 2010. Effect of genome size on AAV vector packaging. Mol Ther 18:80-86.
30. Lai Y, Yue Y, Duan D. 2010. Evidence for the failure of adeno-associated virus serotype 5 to package a viral genome > or =8.2 kb. Mol Ther 18:75-79.
31. Samulski R J, Srivastava A, Berns K I, Muzyczka N. 1983. Rescue of adeno-associated virus from recombinant plasmids: gene correction within the terminal repeats of AAV. Cell 33:135-143.
32. Zhou X, Zeng X, Fan Z, Li C, McCown T, Samulski R J, Xiao X. 2008. Adeno-associated virus of a single-polarity DNA genome is capable of transduction in vivo. Mol Ther 16:494-499.
33. Zhong L, Zhou X, Li Y, Qing K, Xiao X, Samulski R J, Srivastava A. 2008. Single-polarity recombinant adeno-associated virus 2 vector-mediated transgene expression in vitro and in vivo: mechanism of transduction. Mol Ther 16:290-295.
34. Papadakis E D, Nicklin S A, Baker A H, White S J. 2004. Promoters and control elements: designing expression cassettes for gene therapy. Curr Gene Ther 4:89-113.
35. Qing K, Khuntirat B, Mah C, Kube D M, Wang X S, Ponnazhagan S, Zhou S, Dwarki V J, Yoder M C, Srivastava A. 1998. Adeno-associated virus type 2-mediated gene transfer: correlation of tyrosine phosphorylation of the cellular single-stranded D sequence-binding protein with transgene expression in human cells in vitro and murine tissues in vivo. J Virol 72:1593-1599.
36. Mah C, Qing K, Khuntirat B, Ponnazhagan S, Wang X S, Kube D M, Yoder M C, Srivastava A. 1998. Adeno-associated virus type 2-mediated gene transfer: role of epidermal growth factor receptor protein tyrosine kinase in transgene expression. J Virol 72:9835-9843.
37. Heinemeyer T, Wingender E, Reuter I, Hermjakob H, Kel A E, Kel O V, Ignatieva E V, Ananko E A, Podkolodnaya O A, Kolpakov F A, Podkolodny N L, Kolchanov N A. 1998. Databases on transcriptional regulation: TRANSFAC, TRRD and COMPEL. Nucleic Acids Res 26:362-367.
38. Marinescu V D, Kohane I S, Riva A. 2005. MAPPER: a search engine for the computational identification of putative transcription factor binding sites in multiple genomes. BMC Bioinformatics 6:79.
39. Markusic D M, Herzog R W, Aslanidi G V, Hoffman B E, Li B, Li M, Jayandharan G R, Ling C, Zolotukhin I, Ma W, Zolotukhin S, Srivastava A, Zhong L. 2010. High-efficiency transduction and correction of murine hemophilia B using AAV2 vectors devoid of multiple surface-exposed tyrosines. Mol Ther 18:2048-2056.

40. Aslanidi G V, Rivers A E, Ortiz L, Govindasamy L, Ling C, Jayandharan G R, Zolotukhin S, Agbandje-McKenna M, Srivastava A. 2012. High-efficiency transduction of human monocyte-derived dendritic cells by capsid-modified recombinant AAV2 vectors. Vaccine 30:3908-3917.

41. Aslanidi G V, Rivers A E, Ortiz L, Song L, Ling C, Govindasamy L, Van Vliet K, Tan M, Agbandje-McKenna M, Srivastava A. 2013. Optimization of the capsid of recombinant adeno-associated virus 2 (AAV2) vectors: the final threshold? PLoS One 8:e59142.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A recombinant adeno-associated virus (rAAV) particle, comprising:
a viral capsid encapsidating a nucleic acid vector, wherein the nucleic acid vector comprises a glucocorticoid receptor responsive element and/or a transcription factor binding site inserted within an inverted terminal repeat (ITR).

2. The rAAV particle of claim 1, wherein the glucocorticoid receptor responsive element comprises the sequence GGTACANNNTGT(T/C)CT (SEQ ID NO: 1), wherein each N is independently a T, C, G or A and wherein (T/C) is either a T or a C nucleotide, AGAACANNNTGTTCT (SEQ ID NO: 8), or GGCACAGTGTGGTCT (SEQ ID NO:9).

3. The rAAV particle of claim 1, wherein the transcription factor binding site is a transcription factor binding site for POU3F2, FOXJ2, NR2E3, MEF-2, AP-1, Sp-1, KLF-4, GATA-6, HNF-1, MyOD, C/EBP, POU, MRF, NKX2-5, GATA-4, GCM2, OTX-2, Pax-2, or GATA-3.

4. The rAAV particle of claim 1, wherein the nucleic acid vector further comprises a heterologous nucleic acid region comprising a sequence encoding a protein or polypeptide of interest or RNA of interest.

5. The rAAV particle of claim 1, wherein the viral capsid comprises a modified capsid protein comprising at least one mutation.

6. The rAAV particle of claim 1, wherein the nucleic acid vector is single stranded.

7. The rAAV particle of claim 1, wherein the nucleic acid vector is self-complementary.

8. A nucleic acid vector comprising a glucocorticoid receptor responsive element and/or a transcription factor binding site inserted within an inverted terminal repeat (ITR) sequence.

9. The nucleic acid vector of claim 8, wherein the transcription factor binding site is a transcription factor binding site for POU3F2, FOXJ2, NR2E3, MEF-2, AP-1, Sp-1, KLF-4, GATA-6, HNF-1, MyOD, C/EBP, POU, MRF, NKX2-5, GATA-4, GCM2, OTX-2, Pax-2, or GATA-3.

10. The nucleic acid vector of claim 8, wherein the glucocorticoid receptor responsive element comprises the sequence GGTACANNNTGT(T/C)CT (SEQ ID NO: 1), wherein each N is independently a T, C, G or A and wherein (T/C) is either a T or a C nucleotide, AGAACANNNTGTTCT (SEQ ID NO: 8), or GGCACAGTGTGGTCT (SEQ ID NO:9).

11. The nucleic acid vector of claim 8, further comprising a multiple cloning site, a promoter, and/or a heterologous nucleic acid region comprising a sequence encoding a protein or polypeptide of interest or RNA of interest.

12. A kit, comprising the rAAV particle of claim 1 and/or the nucleic acid vector of claim 8.

13. A method of expressing a nucleic acid in a cell comprising:
contacting the cell with the rAAV particle of claim 1, wherein said nucleic acid is expressed in the cell.

14. The method of claim 13, wherein the nucleic acid comprises the ITR sequence comprising the glucocorticoid receptor responsive element and the method further comprises contacting the cell with a glucocorticoid receptor (GR) activator.

15. The method of claim 14, wherein the GR activator is dexamethasone.

16. The method of claim 13, wherein the contacting is in vivo or in vitro.

17. The rAAV particle of claim 1, wherein the particle is of serotype AAV1, AAV2, AAV3, AAV4, AAV5, AAV6, AAV7, AAV8, AAV9, or AAV10.

18. The rAAV particle of claim 17, wherein the ITR is of AAV serotype 2.

19. The rAAV particle of claim 4, wherein the protein or polypeptide of interest is beta-catenin (CTNNB 1), pyruvate dehydrogenase (PDH), parvovirus B19 non-structural protein (B19 NS1), Trichosanthin (TCS), beta-globin (HBB), acid alpha-glucosidase (GAA), Methyl CpG binding protein (MECP2), Aromatic L-amino acid decarboxylase (AADC), Glial cell-derived neurotrophic factor (GDNF), Cystic fibrosis transmembrane conductance regulator (CFTR), Tumor necrosis factor receptor fused to an antibody Fc (TNFR:Fc), HIV-1 gag-proΔrt (tgAAC09), Sarcoglycan, Alpha-1-antitrypsin (AAT), Glutamate decarboxylase 1(GAD1), Glutamate decarboxylase 2 (GAD2), Aspartoacylase (ASPA), Nerve growth factor (NGF), Granulocyte-macrophage colonystimulating factory (GM-CSF), Cluster of Differentiation 86 (CD86 or B7-2), IL-12, neuropeptide Y, ATPase, Ca++ transporting, cardiac muscle, slow twitch 2 (SERCA2), Dystrophin or Minidystrophin, Ceroid lipofuscinosis neuronal 2, Neurturin (NR TN), N-acetylglucosaminidase, alpha (NAGLU), Iduronidase, alpha-1 (IDUA), Iduronate 2-sulfatase (IDS), Glucuronidase, beta (GUSB), Hexosaminidase A, Hexosarninidase B, RPE65, Factor IX, Adenine nucleotide translocator, ApaLI, NADH ubiquinone oxidoreductase subunit 4 (ND4), very long-acyl-CoA dehydrogenase, medium-chain acyl-CoA dehydrogenase (MCAD), M yotubularin 1 (MTM 1), Myophosphorylase (PYGM), Lipoprotein lipase (LPL), sFLTO1, Glucocerebrosidase (GC), UDP glucuronosyltransferase 1 family, polypeptide A1 (UGT1A1), Glucose 6-phosphatase (G6Pase), Ornithine carbamoyltransferase (OTC), Cystathionine-beta-synthase (CBS), Factor VIII (F8), Hemochromatosis (HFE), Low density lipoprotein receptor, Galactosidase, alpha (AGA), Phenylalanine hydroxy lase (P AH), Propionyl CoA carboxylase, alpha polypeptide (PCCA), or myosin 7A (MY07A).

20. The rAAV particle of claim 5, wherein the modified capsid protein comprises at least one of the following mutations:
Y705F, Y731F, or T492V numbered with reference to AAV1,
Y444F+Y500F+Y730F, Y272F+Y444F+Y500F+Y730F+T491 V, or
Y252F+Y272F+Y444F+Y500F+Y704F+7Y30F numbered with reference to AAV2,
Y705F+Y731F, or S663V+T492V numbered with reference to AAV3,
Y719F numbered with reference to AAV5,
Y705F+Y731F, or T492V numbered with reference to AAV6,
Y733F numbered with reference to AAV8, and
Y731F numbered with reference to AAV9.

21. The rAAV particle of claim 4, wherein the protein or polypeptide or RNA of interest is human.

22. The nucleic acid vector of claim 11, wherein the protein or polypeptide of interest is beta-catenin (CTNNB 1), pyruvate dehydrogenase (PDH), parvovirus B19 non-structural protein (B19 NS1), Trichosanthin (TCS), beta-globin (HBB), acid alpha-glucosidase (GAA), Methyl CpG binding protein (MECP2), Aromatic L-amino acid decarboxylase (AADC), Glial cell-derived neurotrophic factor (GDNF), Cystic fibrosis transmembrane conductance regulator (CFTR), Tumor necrosis factor receptor fused to an antibody Fc (TNFR:Fc), HIV-1 gag-proΔrt (tgAAC09), Sarcoglycan, Alpha-1-antitrypsin (AAT), Glutamate decarboxylase 1(GAD1), Glutamate decarboxylase 2 (GAD2), Aspartoacylase (ASPA), Nerve growth factor (NGF), Granulocyte-macrophage colonystimulating factory (GM-CSF), Cluster of Differentiation 86 (CD86 or B7-2), IL-12, neuropeptide Y, ATPase, Ca++ transporting, cardiac muscle, slow twitch 2 (SERCA2), Dystrophin or Minidystrophin, Ceroid lipofuscinosis neuronal 2, Neurturin (NR TN), N-acetylglucosaminidase, alpha (NAGLU), Iduronidase, alpha-1 (IDUA), Iduronate 2-sulfatase (IDS), Glucuronidase, beta (GUSB), Hexosaminidase A, Hexosaminidase B, RPE65, Factor IX, Adenine nucleotide translocator, ApaLI, NADH ubiquinone oxidoreductase subunit 4 (ND4), very long-acyl-CoA dehydrogenase, short-chain acyl-coA dehydrogenase (SCAD), medium-chain acyl-CoA dehydrogenase (MCAD), Myotubularin 1 (MTM 1), Myophosphorylase (PYGM), Lipoprotein lipase (LPL), sFLTO1, Glucocerebrosidase (GC), UDP glucuronosyltransferase 1 family, polypeptide A1 (UGT1A1), Glucose 6-phosphatase (G6Pase), Ornithine carbamoyltransferase (OTC), Cystathionine-beta-synthase (CBS), Factor VIII (F8), Hemochromatosis (HFE), Low density lipoprotein receptor, Galactosidase, alpha (AGA), Phenylalanine hydroxylase (PAH), Propionyl CoA carboxylase, alpha polypeptide (PCCA), or myosin 7A (MY07A).

23. A pharmaceutical composition comprising the recombinant adeno-associated virus (rAAV) particle of claim 1 and a pharmaceutically acceptable carrier.

24. The method of claim 13, wherein the cell is human.

25. The method of claim 24, wherein the cell is a liver cell.

26. The method of claim 16, wherein the contacting is in vivo, and the cell is a human liver cell.

27. The rAAV particle of claim 1, wherein the glucocorticoid receptor responsive element and/or the transcription factor binding site replaces a D-sequence or a portion thereof within the inverted terminal repeat (ITR).

28. The nucleic acid vector of claim 8, wherein the glucocorticoid receptor responsive element and/or the transcription factor binding site replaces a D-sequence or a portion thereof within the inverted terminal repeat (ITR).

29. The method of claim 17, wherein the glucocorticoid receptor responsive element and/or the transcription factor binding site replaces a D-sequence or a portion thereof within the inverted terminal repeat (ITR).

30. The pharmaceutical composition of claim 23, wherein the glucocorticoid receptor responsive element and/or the transcription factor binding site replaces a D-sequence or a portion thereof within the inverted terminal repeat (ITR).

* * * * *

```
                         SEQUENCE LISTING

<160> NUMBER OF SEQ ID NOS: 17

<210> SEQ ID NO 1
<211> LENGTH: 15
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (7)..(9)
<223> OTHER INFORMATION: n is a, c, g, or t

<400> SEQUENCE: 1
ggtacannnt gtyct                                                          15

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2
ctccatcact aggggttcct                                                     20

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
tattagatct gatggccgct                                                     20

<210> SEQ ID NO 4
<211> LENGTH: 125
<212> TYPE: DNA
<213> ORGANISM: Artificial Sequence
<220> FEATURE:
<223> OTHER INFORMATION: Synthetic Polynucleotide

<400> SEQUENCE: 4
ttggccactc cctctctgcg cgctcgctcg ctcactgagg ccgggcgacc aaaggtcgcc         60
cgacgcccgg gctttgcccg ggcggcctca gtgagcgagc gagcgcgcag agagggagtg        120
gccaa                                                                    125

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
aggaacccct agtgatggag                                                     20

<210> SEQ ID NO 6
```

```
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
ctccatcact aggggttcct                                                     20

<210> SEQ ID NO 7
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 7
agtgatggag                                                                10

<210> SEQ ID NO 8
<211> LENGTH: 15
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (7)..(9)
<223> OTHER INFORMATION: n is a, c, g, or t

<400> SEQUENCE: 8
agaacannnt gttct                                                          15

<210> SEQ ID NO 9
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 9
ggcacagtgt ggtct                                                          15

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
tattagatct gatggccgct                                                     20

<210> SEQ ID NO 11
<211> LENGTH: 145
<212> TYPE: DNA
<213> ORGANISM: Artificial Sequence
<220> FEATURE:
<223> OTHER INFORMATION: Synthetic Polynucleotide

<400> SEQUENCE: 11
ttggccactc cctctctgcg cgctcgctcg ctcactgagg ccgggcgacc aaaggtcgcc         60
cgacgcccgg gctttgcccg ggcggcctca gtgagcgagc gagcgcgcag agagggagtg        120
gccaactcca tcactagggg ttcct                                              145
```

```
<210> SEQ ID NO 12
<211> LENGTH: 145
<212> TYPE: DNA
<213> ORGANISM: Artificial Sequence
<220> FEATURE:
<223> OTHER INFORMATION: Synthetic Polynucleotide

<400> SEQUENCE: 12
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc     120
gagcgcgcag agagggagtg gccaa                                           145

<210> SEQ ID NO 13
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 13
ctaggctgta caggatgttc tgcctag                                          27

<210> SEQ ID NO 14
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 14
tcccatagta acgccaatag g                                                21

<210> SEQ ID NO 15
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 15
cttggcatat gatacacttg atg                                              23

<210> SEQ ID NO 16
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 16
ggggaagctc tggatgaaga agtcgct                                          27

<210> SEQ ID NO 17
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 17
agcgacttct tcatccagag cttcccc                                          27
```